(12) United States Patent
Sampson et al.

(10) Patent No.: US 8,802,375 B2
(45) Date of Patent: Aug. 12, 2014

(54) METHODS FOR CHARACTERIZING ANTIBODY BINDING AFFINITY AND EPITOPE DIVERSITY IN FOOD ALLERGY

(75) Inventors: Hugh A. Sampson, Greenwich, CT (US); Jing Lin, Philadelphia, PA (US); Ludmilla Bardina, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 12/880,841

(22) Filed: Sep. 13, 2010

(65) Prior Publication Data

US 2011/0071043 A1  Mar. 24, 2011

Related U.S. Application Data

(60) Provisional application No. 61/242,332, filed on Sep. 14, 2009.

(51) Int. Cl.
  *G01N 33/00* (2006.01)
  *G01N 33/53* (2006.01)

(52) U.S. Cl.
  USPC .......................................... 435/7.1; 435/7.92

(58) Field of Classification Search
  None
  See application file for complete search history.

(56) References Cited

FOREIGN PATENT DOCUMENTS

WO  01/32887  5/2001

OTHER PUBLICATIONS

Wang et al. 'Correlation of IgE/IgG4 milk epitopes and affinity of milk-specific IgE antibodies with different phenotypes of clinical milk allergy.' J. Allergy Clin Immunol. 125:695-702, 2010.*
Lin J et al., "Development of a novel peptide microarray for large-scale epitope mapping of food allergens" Journal of Allergy and Clinical Limmunology, Mosby, Inc., US LNKD-DOI: 10.1016/J. JACI. 2009-05-024, vol. 124, No. 2, Aug. 1, 2009, pp. 315-322.
Matsumoto N. et al., "Peptide array-based analysis of the specific IgE and IgG4 in cow's milk allergens and its use in allergy evaluation" Peptides, Elsevier, Amsterdam LNKD-DOI: 10.1016/J. Peptides, 2009-07-005, vol. 30, No. 10, Jul. 18, 2009, pp. 1840-1847.
Cocco R R et al., "Mutational analysis of immunoglobulin E-binding epitopes of beta-casein and beta-lactoglobulin showed a heterogeneous pattern of critical amino acids between individual patients and pooled sera" Clinical and Experimental Allergy, vol. 37, No. 6, Jun. 2007, pp. 831-838.
Wang J et al.: "Correlation of IgE/IgG4 milk epitopes and affinity of milk-specific IgE antibodies with different phenotypes of clinical milk allergy" Journal of Allergy and Clinical Immunology, Mosby, Inc., US LNKD-DOI: 10.1016/J. JACI. 2009-12-017, vol. 125, No. 3, Mar. 1, 2010, pp. 695-702.
Altschul et al., J. Mol. Biol. 1990; 215: 403.
Berin et al., J Immunol , 161:2561-2566, 1998.
Cariello et al., 1991, Nucleic Acids Res, 19: 4193.
Cerecedo I, Zamora J, Shreffler WG, Lin J, Bardina L, Dieguez MC, et al. Mapping of the IgE and IgG4 sequential epitopes of milk allergens with a peptide microarray-based immunoassay. J Allergy Clin Immunol. 2008; 122:589-94.
Chatchatee P, Jarvinen KM, Bardina L, Beyer K, Sampson HA. Identification of IgE- and IgG-binding epitopes on alpha(s1)-casein: differences in patients with persistent and transient cow's milk allergy. J Allergy Clin Immunol 2001; 107:379-83.
Chatchatee P, Järvinen KM, Bardina L, Vila L, Beyer K, Sampson HA. Identification of IgE and IgG binding epitopes on beta- and kappa-casein in cow's milk allergic patients. Clin Exp Allergy. 2001; 31:1256-62.
Cheng, C.W.; et al. Bioorg. Med. Chem. Lett., 2004, 14, 1987-1990.
Chien et al., 1976, J. Bacteriol, 127: 1550.
Christensen LH, Holm J, Lund G, Riise E, Lund K. Several distinct properties of the IgE repertoire determine effector cell degranulation in response to allergen challenge. J Allergy Clin Immunol. 122(2), 298-304 (2008).
Cocco,R.R., Jarvinen,K.M., Sampson,H.A. and Beyer,K. Mutational analysis of major, sequential IgE-binding epitopes in alpha s1-casein, a major cow's milk allergen Journal J. Allergy Clin. Immunol. 112 (2), 433-437 (2003).
Diaz and Sabino, 1998 Braz J. Med. Res, 31:1239.
El-Khouly F, Lewis SA, Pons L, Burks AW, Hourihane JO. IgG and IgE avidity characteristics of peanut allergic individuals. Pediatr Allergy Immunol 2007; 18:607-13.
Falsey, J.R.; et al. Bioconj. Chem., 2001, 12, 346-353.
Fergusson et al., Pediatrics 86:541-546, 1990.
Flinterman AE, Knol EF, Lencer DA, Bardina L, den Hartog Jager CF, Lin J, et al. Peanut epitopes for IgE and IgG4 in peanut-sensitized children in relation to severity of peanut allergy. J Allergy Clin Immunol. 2008; 121:737-743.
Frank R. The SPOT synthesis technique-Synthetic peptide arrays on membrane supports-principles and applications. J Immunol Methods. Sep. 2002;267(1):13-26.
Hallen,E., Wedholm,A., Andren,A. and Lunden,A. Effect of beta-casein, kappa-casein and beta-lactoglobulin genotypes on concentration of milk protein variants Journal J. Anim. Breed. Genet. 125 (2), 119-129 (2008).
Houseman, B.T.; et al. Langmuir., 2004, 19, 1522-1531.
Houseman, B.T.; et al. Nat. Biotechnol., 2002, 20, 270-274.
Husby et al., Gut, 28:1062-1072, 1987.

(Continued)

*Primary Examiner* — Nora Rooney
(74) *Attorney, Agent, or Firm* — Fish & Richardson P.C.

(57) ABSTRACT

Methods for performing epitope mapping, and for characterizing the antibody binding affinity and epitope diversity of antibodies in a sample using peptide microarray are provided. In some aspects, methods are provided for the specific characterization of IgE and IgG4. Also disclosed are methods for diagnosing whether a milk-allergic individual will outgrow his or her allergy based on the characterization of the individual's milk allergen-specific IgE antibodies.

25 Claims, 12 Drawing Sheets

(56) References Cited

OTHER PUBLICATIONS

Jarvinen KM, Beyer K, Vila L, Chatchatee P, Busse PJ, Sampson HA. B-cell epitopes as a screening instrument for persistent cow's milk allergy. J Allergy Clin Immunol 2002; 110:293-7.
Järvinen KM, Chatchatee P, Bardina L, Beyer K, Sampson HA. IgE and IgG binding epitopes on alpha-lactalbumin and beta-lactoglobulin in cow's milk allergy. Int Arch Allergy Immunol. 2001; 126:111-8.
Juncosa-Ginesta et al., 1994, Biotechniques, 16:820.
Karlin and Altschul, Proc. Natl. Acad. Sci. USA 1990, 87:2264.
Karlin and Altschul, Proc. Natl. Acad. Sci. USA 1993, 90:5873-5877.
Kiyonaka, S.; et al. Nat. Materials, 2004, 3, 58-64.
Lecomte and Doubleday, 1983, Nucleic Acids Res. 11:7505.
Lesaicherre, M. L.; Lue et al.J. Am. Chem. Soc. 2002, 124, 8768-8769.
Lesaicherre, M.L.; et al. Bioorg. Med. Chem. Lett. 2002, 12, 2079-2083.
Lesaicherre, M.L.; et al. Bioorg. Med. Chem. Lett. 2002, 12, 2085-2088.
Lewis SA, Grimshaw KE, Warner JO, Hourihane JO. The promiscuity of immunoglobulin E binding to peanut allergens, as determined by Western blotting, correlates with the severity of clinical symptoms. Clin Exp Allergy 2005; 35:767-73.
Li, S.; et al. Am. Chem. Soc., 2004, 126, 4088-4089.
Lin J, Bardina L, Shreffler WG, Andreae DA, Ge Y, Wang J, et al. Development of a novel peptide microarray for large scale epitope mapping of food allergens. J Allergy Clin Immunol 2009; 124:315-22.
Lin J, Bardina, L, Shreffler WG. Microarrayed allergen molecules for diagnostics of allergy. In: Reineke U., ed. Methods in Molecular Biology- Epitope Mapping Protocols. 524: 259-72 (2008).
Lin J. and Sampson H.A. Immunol 2008; 122:298-304.
Lue, R.Y.P.; et al. J. Am. Chem. Soc., 2004, 126, 1055-1062.
Lundberg et al., 1991, Gene, 108:1.
MacBeath, G.; et al. J. Am. Chem. Soc., 1999, 121, 7967-7968.
Macbeath, G.; Schreiber, S.L. Science, 2000, 289, 1760-1763.
Mayer et al., J. Pediatr. Gastroen. Nutri, 30:S4-S12, 2000.
Mestecky et al., Immunol Allergy Clin N Am, 8:349-368, 1988.
Mita H, Yasueda H, Akiyama K. Affinity of IgE antibody to antigen influences allergen-induced histamine release. Clin Exp Allergy. 2000; 30:1583-9.
Murch, Lancet, 348(9042):1656, 1996.
Myers and Gelfand 1991, Biochemistry 30:7661.
Myers and Miller, CABIOS 1988; 4: 11-17.
Needleman and Wunsch (J. Mol. Biol. 1970, 48:444-453.
Newman, J.R.S.; Keating, A.E. Science, 2003, 300, 2097-2101.
Nordstrom et al., 1981, J. Biol. Chem. 256:3112.
Nowak-Wegrzyn A, Bloom KA, Sicherer SH, Shreffler WG, Noone S, Wanich N. et al., Tolerance to extensively heated milk in children with cow's milk allergy. J Allergy Clin Immunol 2008: 122;342-347.
Oliver, C. et al. Bioconj. Chem., 2003, 14, 430-439.
Panicker et al. (2004) Combinatorial Chemistry & High Throughput Screening, 2004, 7, 547-556.
Pecora V, Nucera E, Schiavino D, Lombardo C, Bardina L, Lin J, et al. Evaluation of specific sequential IgE- and IgG4-binding epitopes, recognized in cow's milk allergic patients during specific oral desensitization, using peptide microarray immunoassay. J Allergy Clin Immunol 2009; 123:S178.
Peeters KA, Koppelman SJ, van Hoffen E, van der Tas CW, den Hartog Jager CG, Penninks AH, et al. Does skin prick test reactivity to purified allergens correlate with clinical severity of peanut allergy? Clin Exp Allergy 2007; 37:108-15.
Reeck et al., Cell 1987; 50: 667.
Salisbury, C. M. et al. J. Am. Chem. Soc. 2002, 124, 14868-14870.
Sampson HA et al., Second symposium on the definition and management of anaphylaxis: Summary report. J Allergy Clin Immunol 2006;117(2):391-7.
Sampson HA, Anaphylaxis and Emergency Treatment, Pediatrics vol. 111 No. 6 Jun. 2003, pp. 1601-1608.
Sampson HA., Food allergy. Part 1: Immunopathogenesis and clinical disorders. J Allergy Clin Immunol 1999; 103:717-28.
Shreffler WG, Beyer K, Chu TH, Burks AW, Sampson HA. Microarray immunoassay: association of clinical history, in vitro IgE function, and heterogeneity of allergenic peanut epitopes. J Allergy Clin Immunol. 2004; 113:776-82.
Shreffler WG, Wanich N, Moloney M, Nowak-Wegrzyn A, Sampson HA. Association of allergen-specific regulatory T cells with the onset of clinical tolerance to milk protein. J Allergy Clin Immunol. 2009; 123:43-52.
Skripak JM, Matsui EC, Mudd K, Wood RA. The natural history of IgE-mediated cow's milk allergy. J Allergy Clin Immunol. 2007; 120:1172-7.
Smith KM et al., Am J Respir Crit. Care Med., 162(4 Pt 2):S175-S178, 2000.
Soellner, M.B.; et al. J. Am.Chem. Soc., 2003, 125, 11790-11791.
Soothill et al., Clin Allergy, 6:305-319, 1976.
Stenesh and McGowan, 1977, Biochim Biophys Acta 475:32.
Stewart,A.F., Bonsing,J., Beattie,C.W., Shah,F., Willis,I.M. and Mackinlay,A.G., Complete nucleotide sequences of bovine alpha S2- and beta-casein cDNAs: comparisons with related sequences in other species Journal Mol. Biol. Evol. 4 (3), 231-241 (1987).
Sudo et al., J. Immunol., 159(4):1739-1745, 1997.
Takagi et al., 1997, Appl. Environ. Microbiol. 63:4504.
Uttamchandani, M.; et al. Bioorg. Med. Chem. Lett., 2003, 13, 2997-3000.
Wanich N, Nowak-Wegrzyn A, Sampson HA, Shreffler WG. Allergen-specific basophil suppression associated with clinical tolerance in patients with milk allergy. J Allergy Clin Immunol 2009; 123:789-94.
Yang et al., J Clin Invest., 106(7):879-886, 2000.
Zhu, Q.; et al.. Org. Lett., 2003, 5, 1257-1260.

* cited by examiner

α$_{S1}$ Casein

RPKHPIKHQGLPQEVLNENLLRFFVAEFPEVFGKEKVNELSKDIGSESTE

DQAMEDIKQMEAESISSSEEIVPNSVEQKHIQKEDVPSERYLGYLEQLLR

LKKYKVPQLEIVPNSAEERLHSMKEGIHAQQKEPMIGVNQELAYFYPELF

RQFYQLDAYPSGAWYYVPLGTQYTDAPSFSDIPNPIGSENSEKTTMPLW

α$_{S2}$ Casein

KNTMEHVSSSEESIISQETYKQEKNMAINPSKENLCSTFCKEVVRNANEE

EYSIGSSSEESAEVATEEVKITVDDKHYQKALNEINQFYQKFPQYLQYLY

QGPIVLNPWDQVKRNAVPITPTLNREQLSTSEENSKKTVDMESTEVFTKK

TKLTEEEKNRLNFLKKISQRYQKFALPQYLKTVYQHQKAMKPWIQPKTKV

IPYVRYL

β Casein

RELEELNVPGEIVESLSSSEESITRINKKIEKFQSEEQQQTEDELQDKIH

PFAQTQSLVYPFPGPIPNSLPQNIPPLTQTPVVVPPFLQPEVMGVSKVKE

AMAPKHKEMPFPKYPVEPFTESQSLTLTDVENLHLPLPLLQSWMHQPHQP

LPPTVMFPPQSVLSLSQSKVLPVPQKAVPYPQRDMPIQAFLLYQEPVLGP

VRGPFPIIV

β Lactoglobulin

LIVTQTMKGLDIQKVAGTWYSLAMAASDISLLDAQSAPLRVYVEELKPTP

EGDLEILLQKWENDECAQKKIIAEKTKIPAVFKIDALNENKVLVLDTDYK

KYLLVCMENSAEPEQSLVCQCLVRTPEVDDEALEKFDKALKALPMHIRLS

FNPTQLEEQCHI

κ Casein

QEQNQEQPIRCEKDERFFSDKIAKYIPIQYVLSRYPSYGLNYYQQKPVAL

INNQFLPYPYYAKPAAVRSPAQILWQVLSNTVPAKSCQAQPTTMARHPH

PHLSFMAIPPKKNQDKTEIPTINTIASGEPTSTPTTEAVESTVATLEDSP

EVIESPPEINTVQVTSTAV

METHODS FOR CHARACTERIZING ANTIBODY BINDING AFFINITY AND EPITOPE DIVERSITY IN FOOD ALLERGY

RELATED APPLICATIONS

The present application claims the benefit of U.S. Provisional Patent Application Ser. No. 61/242,332, filed Sep. 14, 2009, which is herein incorporated by reference in its entirety.

STATEMENT REGARDING FEDERALLY SPONSORED RESEARCH OR DEVELOPMENT

The United States Government has certain rights to this invention by virtue of funding received from the National Institute of Health/National Institute of Allergy and Infectious Diseases; Grant No. AI-44236.

REFERENCE TO SEQUENCE LISTING

Pursuant to 37 C.F.R. 1.821(c), a sequence listing is submitted herewith via EFS-Web as an ASCII compliant text file named "SequenceListing.txt" that was created on May 3, 2012, and has a size of 11,984 bytes. The content of the aforementioned file named "SequenceListing.txt" is hereby incorporated by reference in its entirety.

FIELD OF THE INVENTION

The present invention relates to methods for performing epitope mapping, and for characterizing the antibody binding affinity and epitope diversity of antibodies in a sample using peptide microarray. In some aspects, methods are provided for the specific characterization of IgE and IgG4. The invention also provides methods for diagnosing whether a milk-allergic individual will outgrow his or her allergy based on the characterization of the individual's milk allergen-specific IgE antibodies.

BACKGROUND OF THE INVENTION

It is estimated that food allergies affect at least 12 million Americans, and the prevalence is rising. Food allergies cause roughly 30,000 emergency room visits and 100 to 200 deaths per year in the United States. Six (6) to 8 percent of children under the age of three have food allergies and nearly four percent of adults have them [National Institute of Allergy and Infectious Diseases (July 2004); "Food Allergy: An Overview" (PDF); National Institutes of Health. pp. 35]. The most common food allergies in adults are shellfish, peanuts, tree nuts, fish, and eggs, and the most common food allergies in children are milk, eggs, peanuts, and tree nuts [id.].

Cow's milk hypersensitivity is a common disease affecting 2.5% of infants in the first year of life in prospective studies [1], with approximately 60% of these milk disorders due to IgE-mediated mechanisms. Although the majority of children with IgE-mediated milk allergy develop tolerance by their teenage years [2], 15-20% have lifelong allergy. The mechanisms responsible for tolerance are still not clearly understood; it has been shown that the presence of IgE antibodies to distinct allergenic epitopes of cow's milk proteins can be used as a marker of persistent allergy [3]. Furthermore, a recent study demonstrated that the majority of milk allergic children can tolerate extensively heated forms of milk, and this subset of milk allergic patients are more likely to become tolerant to milk over time [4].

The current diagnostic modalities for food allergy include skin prick testing and measurement of serum specific IgE levels. These results give an indication of the likelihood of clinical reactivity, however, individual results do not provide prognostic information or distinguish between the different phenotypes of food allergy. The importance of sequential epitope recognition in the persistence of cow's milk allergy has been highlighted in several studies utilizing SPOTS membrane technology [5-7]. However, this method is time and labor intensive. Recently, peptide microarrays have been developed for large-scale epitope mapping using small quantities of serum. Shreffler et al. [8] used the peptide microarray immunoassay to examine serum samples from peanut allergic patients and confirmed that antigenic areas identified by this method correlated with areas defined by SPOTS membrane mapping. Furthermore, epitope recognition correlated with peanut allergy severity [8,9].

Similarly, peptide microarray results have been shown to correlate with clinical features of milk allergy. Milk allergic and tolerant patients demonstrated different epitope recognition patterns, with allergic patients having higher ratios of IgE to IgG4 binding than those tolerant to milk [10]. Decreases in IgE binding and increases in IgG4 binding to milk peptides were correlated with clinical improvement in children undergoing oral immunotherapy with milk [11]. Differences in epitope diversity appear to be associated with clinical features of food allergy. Studies of milk allergenic epitopes have further demonstrated that certain milk IgE epitopes may be used as candidate biomarkers to predict the development of tolerance to milk.

However, the use of IgE epitopes alone as biomarkers may not be sufficient to reliably predict whether an allergic individual will outgrow his or her allergy to milk. Moreover, characterization of allergenic epitopes can lead to a better understanding of the pathogenesis and tolerance induction of food allergy. Therefore, what is needed in the art are methods that provide greater specificity, reliability and efficiency for making such predictions and for characterizing allergenic epitopes. The present invention provides such methods.

SUMMARY OF THE INVENTION

In certain aspects, the present invention is directed to a method for determining antibody binding affinity to an allergen in an antibody-containing sample from a subject, which includes: (a) obtaining the antibody-containing sample from the subject; (b) incubating the sample with a peptide library corresponding to the allergen immobilized on a solid support, wherein the peptide library includes at least one allergen epitope to form an incubation mixture; (c) incubating a first portion of the incubation mixture with a competitor, wherein the competitor includes at least one epitope of the allergen, and incubating a second portion of the incubation mixture under the same conditions but in the absence of the competitor; (d) detecting antibody binding to the peptide library in the first and second portions of the incubation mixture; and (e) comparing the number of subject antibodies that remain bound to the at least one epitope in the first and second portions of the incubation mixture to determine the affinity of antibody binding to the immobilized allergen epitopes.

In certain embodiments of the invention, a method of allergy treatment prognosis in a subject having an allergic reaction to an allergen is provided, the method including determining whether the subject contains antibodies having a higher affinity for the allergen as compared to a subject that does not have an allergic reaction to the allergen. In some aspects, the affinity for the allergen is determined using the following steps: obtaining the antibody-containing sample from the subject; incubating the sample with a peptide library corresponding to the allergen immobilized on a solid support, wherein the peptide library includes at least one allergen epitope to form an incubation mixture; incubating a first portion of the incubation mixture with a competitor, wherein the competitor includes at least one epitope of the allergen, and incubating a second portion of the incubation mixture under the same conditions but in the absence of the competitor; detecting antibody binding to the peptide library in the first and second portions of the incubation mixture; and comparing the number of subject antibodies that remain bound to the at least one epitope in the first and second portions of the incubation mixture to determine the affinity of antibody binding to the immobilized allergen epitopes.

In some aspects, the present invention provides a method for diagnosing whether a milk allergic child is likely to outgrow a milk allergy, which method includes: obtaining an antibody-containing sample from the subject; incubating the sample with a peptide library corresponding to the allergen immobilized on a solid support, wherein the peptide library includes at least one milk allergen epitope to form an incubation mixture; incubating a first portion of the incubation mixture with a competitor, wherein the competitor includes at least one epitope of the allergen, and incubating a second portion of the incubation mixture under the same conditions but in the absence of the competitor; detecting IgE antibody binding to the at least one epitope in the first and second portions of the incubation mixture; comparing the number of subject IgE antibodies that remain bound to the at least one epitope in the first and second portions of the incubation mixture to determine the affinity of IgE antibody binding to the immobilized allergen epitopes; comparing the IgE epitope binding affinity to a reference profile of IgE epitope hotspots; and diagnosing that the subject is not likely to outgrow the milk allergy if any of the individual's IgE antibodies bind one or more of the IgE epitope hotspots in the reference profile with high affinity.

In certain aspects of the present invention, at least one IgE epitope is selected from the group consisting of FPEVFGKEKVNELSKDI (SEQ ID NO: 6); QKHIQKEDVPSERYLGYL (SEQ ID NO: 7); LEIVPNSAEERLHS (SEQ ID NO:8); AWYYVPLGTQYTDAPSF (SEQ ID NO: 9); INPSKENLCSTFCKEVV (SEQ ID NO: 10); EVDDEALEKFDKAL (SEQ ID NO: 11); RFFSDKIAKYIPIQYVL (SEQ ID NO: 12); DSPEVIESPPEINTVQV (SEQ ID NO: 13); CKEVVRNANEEEYS (SEQ ID NO: 14); and QTPVVVPPFLQPEV (SEQ ID NO: 15).

In other aspects, the peptide library includes a series of overlapping peptides, the peptides being fragments of the milk allergen, wherein the overlapping peptides comprise epitopes from the milk allergen, and wherein the milk allergen is one or more of the allergens selected from the group consisting of αS1-casein, αS2-casein, κ-casein, β-casein, and β-lactoglobulin.

In yet other aspects, the competitor is selected from the group consisting of αS1-casein, αS2-casein, κ-casein, β-casein, and β-lactoglobulin.

In certain embodiments of the invention, a kit for diagnosing whether a milk allergic subject is likely to outgrow a milk allergy, is provided, the kit providing: a microarray slide comprising a peptide library derived from at least one milk allergen selected from the group consisting of αS1-casein, αS2-casein, κ-casein, β-casein, and β-lactoglobulin; a competitor, wherein the competitor includes at least one milk allergen selected from the group consisting of αS1-casein, αS2-casein, κ-casein, β-casein, and β-lactoglobulin; a detection system; a positive control (such as, e.g., a serum pool); and, optionally instructions for use comprising an IgE epitope hotspot reference profile, wherein the reference profile identifies IgE epitopes that indicate a patient is unlikely to outgrow his or her milk allergy, if his or her IgE antibodies bind one or more of the epitopes with high affinity.

In certain aspects, the competitor in the kit is provided as a solution. In other aspects, the competitor is lyophilized. In some aspects, the kit further includes a blocking reagents comprising human serum albumin. In other aspects, the kit provides an appropriate buffer. In some aspects, the competitor is in a solution comprising 1% HSA in PBST. In still other aspects, the detection system of the kit includes a secondary antibody and a dendrimer.

In one embodiment of the invention, a method of identifying an epitope hotspot in an allergic population is provided, wherein the allergic population is allergic to one or more allergens, which includes: obtaining an antibody-containing sample from three or more individuals of the allergic population as a test sample and from three or more individuals in a non-allergic population as a control sample; incubating each of the test and control samples with a peptide library immobilized on a solid support to form an incubation mixture, wherein the peptide library includes at least one allergen epitope; incubating a first portion of the incubation mixture of the test and the control samples with a competitor, wherein the competitor is derived from the one or more allergens; and incubating a second portion of the incubation of the test and control samples in the absence of the competitor; detecting antibody binding to the at least one epitope in the first and second incubation portions of the test and control samples; comparing the number of subject antibodies that remain bound to the at least one epitope in the test group and in the control group in each of the first and second incubation portions to determine the affinity of antibody binding to the immobilized allergen epitopes; and identifying which of the allergen epitopes are epitope hotspots, wherein the epitope hotspots are bound by antibody in a majority of the test samples; and wherein the epitope hotspots are bound with a higher affinity in the test samples compared to the control samples.

In certain aspects of the invention, the identified epitope hotspots are assembled as an epitope hotspot reference profile. In other aspects, the control sample is derived from a subject selected from the group consisting of a non-milk-allergic subject, a subject who has outgrown an allergy to milk, and a heated-milk tolerant subject.

In some embodiments of the invention, an IgE epitope hotspot reference profile comprising amino acid sequences of one or more IgE epitopes selected from the group consisting of FPEVFGKEKVNELSKDI (SEQ ID NO: 6); QKHIQKEDVPSERYLGYL (SEQ ID NO: 7); LEIVPNSAEERLHS (SEQ ID NO:8); AWYYVPLGTQYTDAPSF (SEQ ID NO: 9); INPSKENLCSTFCKEVV (SEQ ID NO: 10); EVDDEALEKFDKAL (SEQ ID NO: 11); RFFSDKIAKYIPIQYVL (SEQ ID NO: 12); DSPEVIESPPEINTVQV (SEQ ID NO: 13); CKEVVRNANEEEYS (SEQ ID NO: 14); and QTPVVVPPFLQPEV (SEQ ID NO: 15).

In some aspects, an antibody binds an epitope with high affinity if the strength of antibody binding has a Z score that is greater than 3 and the Z score decreases less than about 50 percent in the first portion as compared to the second portion of the incubation mixture.

In some aspects, the binding of the antibody from the sample of the subject is carried out on a microarray immunoassay. In other aspects, concentration of the competitor ranges from about 0.1 to about 10 mg/ml.

In certain embodiments, the allergen is selected from the group consisting of αS1-casein, αS2-casein, κ-casein, β-casein, and β-lactoglobulin. In other embodiments, the competitor is selected from the group consisting of αS1-casein, αS2-casein, κ-casein, β-casein, and β-lactoglobulin.

In some aspects, the peptide library includes a series of overlapping peptides, the peptides being fragments of the allergen, wherein the overlapping peptides comprise epitopes from the allergens. The peptides can range from about 5 to about 50 and from about 10 to about 30 amino acids in length.

In certain embodiments, the allergen is two or more allergens. In other embodiments, the antibody is selected from the group consisting of IgM, IgD, IgG1, IgG2, IgG3, IgG4, IgE, IgA1 and IgA2.

In certain aspects of the invention, the incubation step wherein the sample is incubated with the immobilized peptide library is carried out at a temperature ranging from about 0 to about 15 degrees Celsius. In other aspects, this incubation step is carried out at a temperature of 4 degrees Celsius. In some aspects, this incubation step is carried out for at least about 5 minutes, for at least about 1 hour or at least 24 hours. In yet other aspects, the incubation step, in which the competitor is incubated with the immobilized peptide library, is carried out at a temperature in the range of about 4 to about 50 degrees Celsius. In still other aspects, the incubation step, in which the competitor is incubated with the immobilized peptide library, is carried out at a temperature of about 16 degrees Celsius.

In certain embodiments, the detecting step of the assays of the invention includes: incubating the peptide library with a secondary antibody, wherein the secondary antibody is able to specifically bind the subject antibody; and incubating the peptide library with a fluorescently-labeled dendrimer, wherein the dendrimer is capable of specifically binding the secondary antibody. In other embodiments, the secondary antibody binds to the constant region of the subject antibody. In yet other embodiments, incubation of the secondary antibody is carried out at about 4 degrees Celsius. In certain aspects, the incubation with dendrimer is carried out at about 31 degrees Celsius.

In some aspects, the affinity of antibody binding is determined by calculating a Z score of antibody binding to the at least one epitope is the first and second incubation mixtures, wherein the antibody is a high affinity antibody if the Z score is greater than three and the difference between the first and second incubation portions is less than about 50 percent.

In certain embodiments, the subject is a mammal, a human patient, or a child.

In one aspect of the present invention, a peptide sequence of the peptide library is about 20 amino acid residues in length.

In certain aspects of the invention, the allergen is a food allergen. In some aspects, the allergen is derived from a legume, a tree nut, a cereal grain, a fruit, a vegetable, a seed, a fish, a crustacean, a mollusk, poultry and a dairy product.

These and other aspects of the present invention will be apparent to those of ordinary skill in the art in light of the present specification, claims and drawings.

BRIEF DESCRIPTION OF THE DRAWINGS

FIG. 3. Amino acid sequence of milk allergens. The full length amino acid sequences set forth in FIG. 3 have the following sequence identifiers: $α_{s1}$ Casein (SEQ ID NO: 1); $α_{s2}$ Casein (SEQ ID NO: 2); β Casein (SEQ ID NO: 3), β Lactoglobulin (SEQ ID NO: 5), and κ Casein (SEQ ID NO: 4). Candidate peptide amino acid sequences of informative epitopes identified based on the binding frequency are in bold and underlined. Informative epitopes recognized by >50% of the allergic patients with high affinity IgE antibodies are boxed. The numbers and letters indicated on top of each epitope correspond to the ones indicated in the other Figures and correspond to the following SEQ ID NOs: epitope 1: SEQ ID NO: 6; epitope 2: SEQ ID NO: 7; epitope 3: SEQ ID NO: 8; epitope 4: SEQ ID NO: 9; epitope 5: SEQ ID NO: 10; epitope 6/C: SEQ ID NO: 11; epitope 7/D: SEQ ID NO: 12; epitope 8/E: SEQ ID NO: 13; epitope A: SEQ ID NO: 14; epitope B: SEQ ID NO: 15.

DETAILED DESCRIPTION

Figure 1:
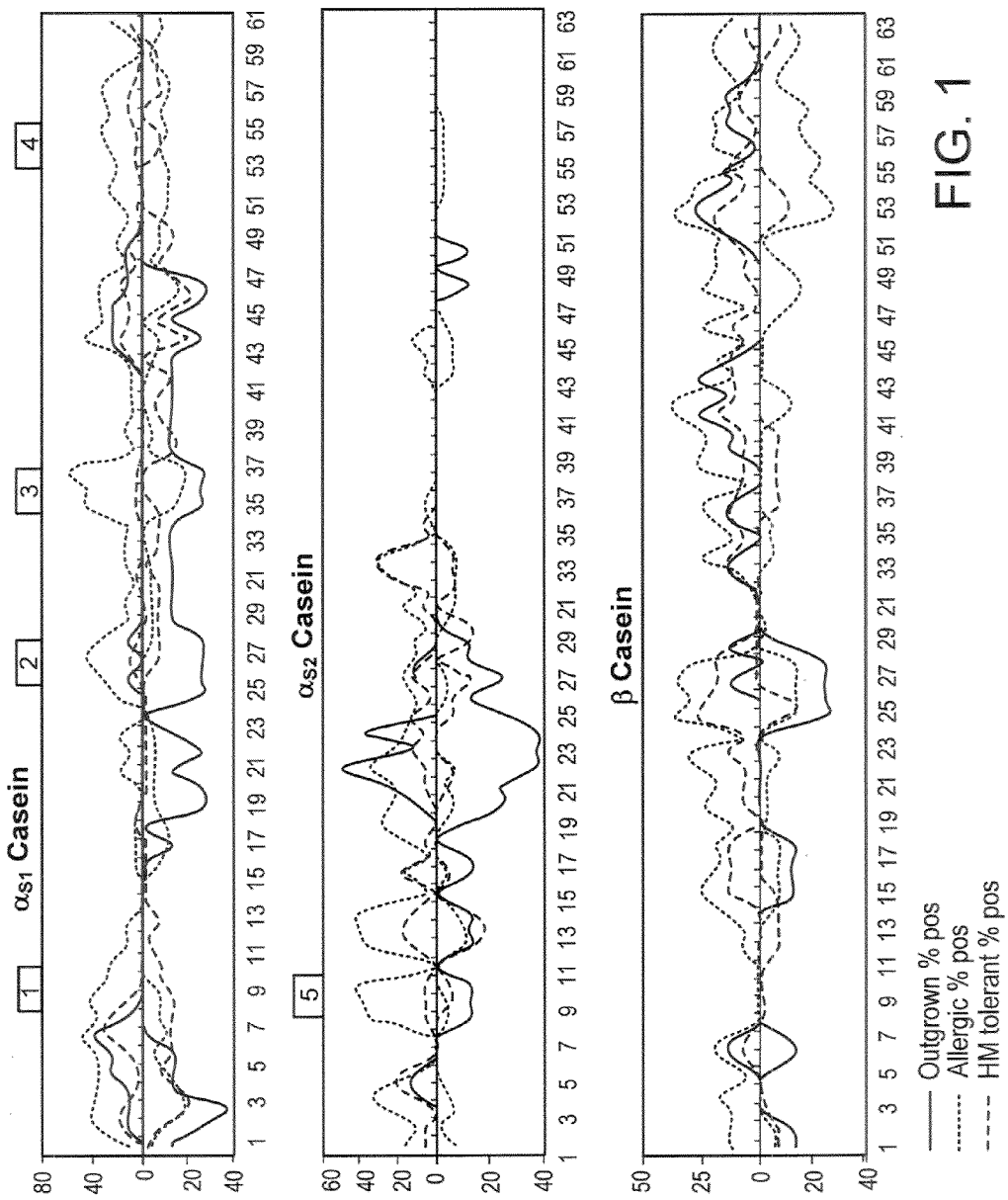
FIG. 1. Comparison of IgE and IgG4 binding frequency to peptides of five milk allergens between the different clinical groups. The x-axis shows the overlapping peptides and the y-axis shows the percentage of patients within each group showing positive binding to each peptide. IgE data are shown on the upper half while IgG4 data are shown in reverse order on the lower half. Candidates of informative epitopes are indicated with numbers (Nos. 1-8).
Figure 1:
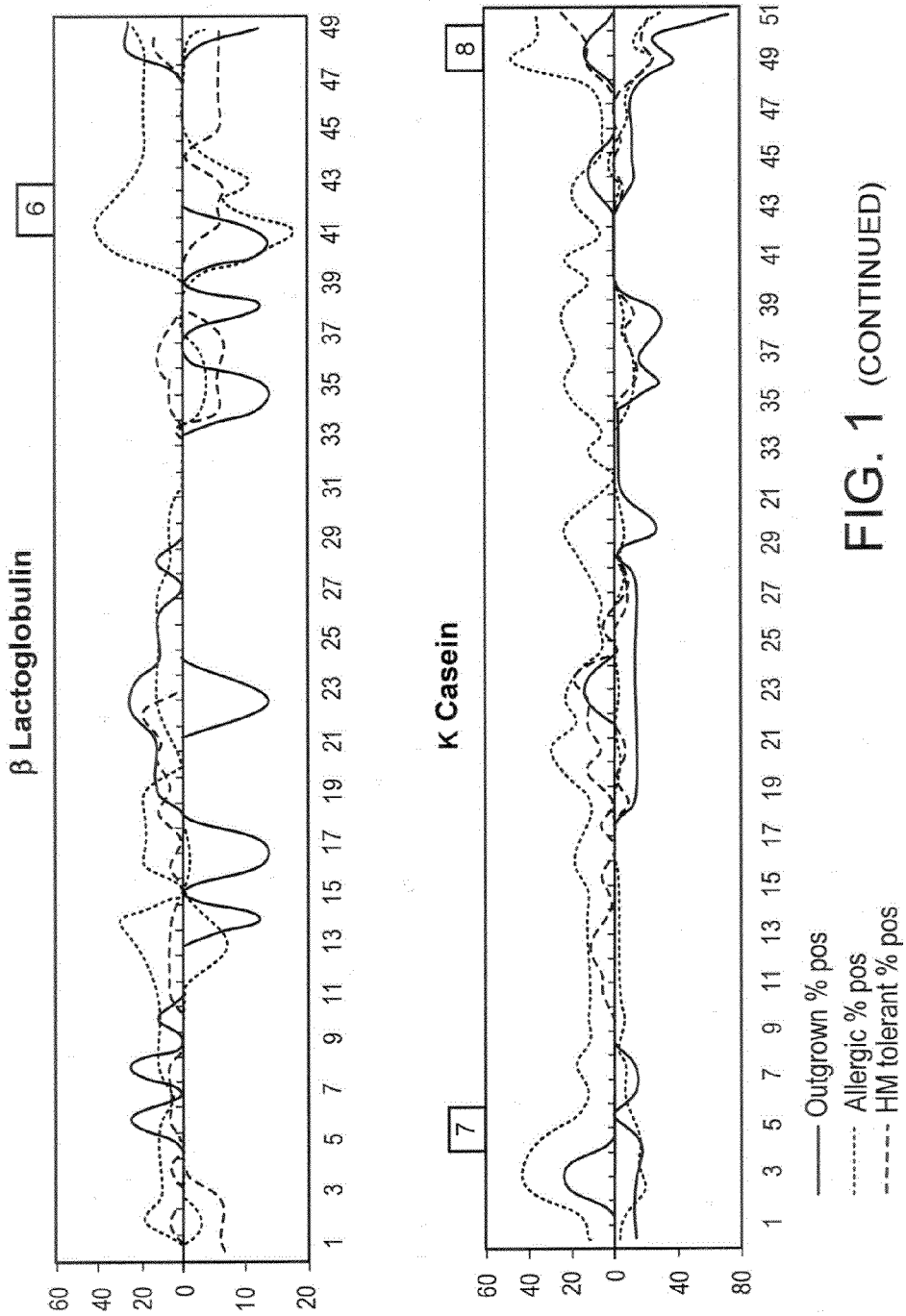

The following definitions are provided for clarity and illustrative purposes only, and are not intended to limit the scope of the invention.

In certain aspects of the invention, methods are provided for measuring antibody binding affinity to epitopes of an allergen using a competitive inhibition assay. Preferably, the epitopes from the allergen are arrayed on a solid support such as a microarray and the affinity of the antibody binding from the serum or other antibody-containing sample of a subject is determined using a microarray-based competitive inhibition immunoassay.

In certain embodiments, the present invention relates to the surprising discovery using a peptide microarray-based immunoassay that immunoglobulin (Ig)E affinity, as well as epitope diversity, correlate with clinical phenotypes and severity of milk allergy. Specifically, patients with persistent allergy, i.e. those who could not tolerate extensively heated milk protein, had increased epitope binding affinity as compared to those with transient allergy (outgrown and those who were HM tolerant). These patient also had increased epitope diversity compared to those with transient allergy.

In certain aspects, the microarray-based competitive inhibition immunoassay (assay) of the invention is useful for measuring the affinity of IgE. In other aspects, IgM, IgD, IgG, and IgA affinity may also be measured. In preferred embodiments, the allergen is a protein. In other preferred embodiments, the epitopes from the protein are arrayed on a solid support as a series of overlapping peptide fragments of the allergen. More preferably, IgE from the serum of the subject binds to sequential epitopes on the allergen, and the microarray is comprised of sequential overlapping epitopes from the allergen.

The methods provide for spotting of microarray slides with a peptide library. In a specific embodiment, the peptide library includes peptides corresponding to amino acid sequences found in milk allergens. However, peptide libraries of other allergens, such as other food allergens, e.g., egg, peanut, tree nut, fish, shellfish, soy, or wheat allergens are also contemplated by the present invention. In other aspects, the libraries can be derived from allergens derived from a legume, a tree nut, a cereal grain, a fruit, a vegetable, a seed, a fish, a crustacean, a mollusk, poultry and a dairy product. Further, some of the peptides in the peptide libraries of the invention constitute partial or complete antibody epitopes.

In general, allergen peptide libraries contain peptide fragments of allergenic proteins. Typically, these peptide fragments have sequences that overlap each other. Further, these peptide fragments contain partial or complete epitopes that are bound by antibodies specific for the particular allergenic protein or proteins from which the peptide fragments are derived. It is well known in the art how to generate a peptide library based on the sequence of one or more proteins. Thus, a peptide library of any of the food allergens, e.g., peanut, shrimp, milk, etc. of the present invention may easily be generated.

In a specific embodiment, the allergen is a milk allergen selected from the group consisting of αS1-casein, αS2-casein, κ-casein, β-casein, and β-lactoglobulin. More particularly, the method includes the binding of IgE from the serum of the subject to the milk allergen on a microarray immunoassay, wherein the microarray includes an array of overlapping peptides from one or more of the allergens αS1-casein, αS2-casein, κ-casein, β-casein, and β-lactoglobulin.

In other aspects of the invention, methods are provided for measuring antibody binding affinity and epitope diversity. In a specific embodiment of the invention, the epitope diversity of milk allergen-specific IgE and the binding affinity of the milk-allergen specific IgE is determined by the microarray-based assays of the invention.

In other embodiments of the present invention, methods are provided for identifying "epitope hotspots" using the microarray-based competitive inhibition assays of the invention. In other embodiments, the epitope hotspots identified by the present methods are used to compile a reference profile. In a specific embodiment of the invention, a reference profile of milk allergen-specific IgE epitope hotspots is provided.

In yet other aspects of the invention, prognostic methods are provided for determining whether an individual will outgrow his or her allergy to milk based on a comparison of the individual's milk allergen-specific IgE binding affinity to an IgE epitope hotspot reference profile.

The current diagnostic tools are unable to provide this type of prognostic information, therefore, the methods using peptide microarray-based assays, as provided by the present invention are a much needed advancement in diagnostics for the field of allergy. The diagnostic methods of the present invention are contemplated for use to diagnose food allergy in both adults and children.

It would be particularly useful to be able to provide a prognosis for whether a patient is likely to outgrow his or her food allergy. If a patient is diagnosed as not likely to outgrow a food allergy, then the treatment of the patient may be adjusted accordingly. This is because individuals with a food allergy that will not be outgrown may need to be treated. At the present time there are no approved forms of treatment for food allergy. However, several immunotherapeutic approaches are being studied and should be available in the next several years. Consequently, young children who are identified with persistent food allergy would be started on immunotherapy because studies suggest that earlier immunotherapeutic intervention is more effective in reversing allergic responses.

Immune Responses and Allergy

IgE-mediated hypersensitivity mechanisms account for the majority of food-related allergic disorders. For example, approximately 2.5% of infants are born with an allergy to milk. 15% of infants with IgE-mediated cow milk allergy retain mil product sensitivity into the second decade, 35% develop allergic reactions to other foods, and about 60% develop respiratory allergy. The increased susceptibility of young infants to food allergic reactions is believed to result from immaturity of the immune system and gastrointestinal tract. The gastrointestinal tract forms a barrier to the outside environment and provides a surface to process and absorb ingested food, and to discharge waste products. The immune system associated with this barrier, the gut-associated lymphoid tissue [GALT], is capable of discriminating between harmless foreign proteins and commensal organisms, and dangerous pathogens.

The mucosal immune system is comprised of both the innate and adaptive immune systems. Gut epithelial and mucosal cells, which form a major portion of the mucosal innate immune system, are well suited to initiate protective responses. Unlike the systemic immune system, the adaptive mucosal immune system is specifically proficient at inhibiting responses to non-dangerous antigens [oral tolerance] and yet mounting a rapid response to pathogens. However, developmental immaturity of various components of the gut barrier [e.g., decreased stomach acidity and intestinal and pancreatic enzyme activity, immature glycocalyx, and the like] and immune system reduces the efficiency of the infant mucosal barrier, and likely plays a major role in the increased prevalence of gastrointestinal infections and food allergy seen in the first few years of life. The early introduction of numerous food antigens has been shown to stimulate excessive production of IgE antibodies (Soothill et al., Clin Allergy, 6:305-319, 1976) and induce allergic conditions in genetically predisposed infants. (Fergusson et al., Pediatrics 86:541-546, 1990).

The GALT is comprised of four distinct lymphoid compartments: Peyer's patches and the appendix, lamina propria lymphocytes and plasma cells, intra-epithelial lymphocytes, and mesenteric lymph nodes (Mayer et al., J. Pediatr. Gastroen. Nutri, 30:S4-S12, 2000). M cells, specialized epithelial cells overlying Peyer's patches, sample antigens [e.g., foreign proteins] from the gut lumen, especially large particulate antigens and a number of bacteria and viruses, and pass them intact to underlying macrophages. Macrophages process and present these antigens to resident precursor T cells and B cells, which become activated and then "home" to other areas of the mucosal immune system. Local B cells produce secretory-IgA antibodies [S-IgA], which are actively transported into intestinal secretions forming a component of the protective barrier (Mestecky et al., Immunol Allergy Clin N Am, 8:349-368, 1988).

Despite the evolution of an elegant barrier system, about 2% of ingested food antigens are absorbed and transported throughout the body in an "immunologically" intact form, even through the mature gut (Husby et al., Gut, 28:1062-1072, 1987). Recent studies in rodent models have demonstrated the presence of $Fc\epsilon II$ receptors on gut epithelial cells that facilitate antigen-specific transport [10-times faster] in IgE-sensitized rats as compared to non-sensitized controls (Berin et al., J. Immunol., 161:2561-2566, 1998; Yang et al., J Clin Invest., 106(7):879-886, 2000).

As noted, intact food antigens penetrate the gastrointestinal tract and enter the circulation in both normal children and adults. However, these intact proteins generally do not cause clinical symptoms because most individuals develop tolerance to ingested antigens. In mucosal tissues, soluble antigens, such as food antigens, are typically poor immunogens and induce a state of unresponsiveness known as "oral tolerance." Unresponsiveness of T cells to ingested food proteins is believed to be the result of T cell anergy and/or induction of regulatory T cells. Intestinal epithelial cells [IECs] play a major role in tolerance induction to food antigens, acting as non-professional antigen presenting cells (Mayer et al., J. Pediatr. Gastroen. Nutri, 30:S4-S12, 2000). In addition, dendritic cells residing within the non-inflammatory environment of Peyer's patches express IL-10 and IL-4, which favor generation of tolerance. T regulatory cells [Th3 and Tr-1 cells], which are potent sources of TGF-$\beta$. (Smith et al., Am J Respir Crit. Care Med., 162(4 Pt 2):5175-5178, 2000) are generated in mucosal lymphoid tissue in response to low-dose antigen and mediate "bystander tolerance" within the GI tract. The gut flora also is believed to play a significant role in the induction of oral tolerance since animals raised in a germ-free environment from birth fail to develop normal tolerance (Sudo et al., J. Immunol., 159(4):1739-1745, 1997). The generation of regulatory T cells appears to require a threshold level of inflammatory response to bacterial challenge (Murch, Lancet, 348(9042):1656, 1996). In a specific embodiment of the invention, an individual who does not mount an allergic response to heated cow's milk is said to be "tolerant" to heated cow's milk.

The development of an IgE-mediated response to an allergen [generally a glycoprotein] is the result of a series of molecular and cellular interactions involving antigen-presenting cells [APCs], T cells, and B cells. APCs [dendritic cells, activated B cells] present small peptide fragments [T cell epitopes] in conjunction with MHC class II molecules to T cells. T cells bearing the appropriate complementary T cell receptor [TCR] will bind to the peptide-MHC complex. This interactive "first signal" leads to T cell proliferation and cytokine generation and the generation of a "second" signal, which promotes an IgE response [Th2 lymphocyte activation]. When antigen becomes bound to surface immunoglobulin on B cells, the cell is activated and processes antigen for expression of peptides bound to MHC class II molecules. T cells and their products will in turn interact with B cells bearing appropriate antigen-specific receptors leading to isotype switching and the generation of antigen-specific IgE. At all stages, a number of specific cytokines are secreted which modulate the cell interactions. The antigen-specific IgE then binds to surface receptors of mast cells, basophils, macrophages, and other APCs, aiming the immune system for an allergic reaction with the next encounter of the specific antigen.

The next and subsequent encounters of the specific antigen trigger an immunological cascade that results in the manifestations of an allergic response. In some individuals, the subsequent responses may be severe, even to the level of being threatening; in other individuals, the response may be less severe. In certain embodiments, the present invention is designed to assess the degree of antibody binding affinity that the IgE of a subject exhibits. As described in the Examples herein below, it has been determined that the greater the degree of antibody affinity against certain or specific allergenic epitopes, the greater the severity of the clinical symptoms of the allergy and the less likely it is that the subject will outgrow the allergy.

Examples of allergic diseases which may be characterized by the methods of the present invention include but are not limited to milk allergy, soy allergy, peanut allergy, egg allergy, shellfish (e.g., shrimp), and other food allergies.

An allergy is an immune system reaction to a typically harmless substance. The immune system is always working to fight off parasites, fungi, viruses and bacteria. However, sometimes the immune system will treat a harmless substance (called an allergen) as an unwanted invader and try to fight it. This overreaction of the body's immune system to a typically harmless substance is called an allergic reaction. Different allergies have different names, according to where they occur in the body. There are five common types of allergies, namely, allergic rhinitis, allergic dermatitis, asthma, food allergies and urticaria. Food allergies affect the stomach and other internal organs, and may also cause symptoms to the entire body.

Almost anything can act as an allergen. However, some substances are very common allergens, such as, pollen and mold, dust mite droppings, pet allergens, various foods, insect stings, and cockroach sensitivities. Sensitivities to certain foods affect 6-8% of children and 1-2% of adults. Ninety (90) percent of all food allergies are caused by eight types of food; namely, milk, soy, eggs, wheat, peanuts, tree nuts, fish and shellfish. A few food preservatives, such as monosodium glutamate (found in many Asian foods, bouillon cubes and other preserved meat products) and metabisulfites (found in wines, particularly red wines) also cause allergic reactions.

While in preferred embodiments the allergen is a protein, it is contemplated that the immunoassays may be carried out with non-protein allergens also. In specific embodiments, the allergen is preferably a food allergen, although the methods of the invention may be applicable to other allergens, e.g., environmental allergens (e.g., pollen) or an allergen from pet dander. The food allergen may be from any food group. For example, the food allergen is selected from the group consisting of an allergen from a legume (e.g., peanut; soybean, green pea); an allergen from a tree nut (e.g., brazil nut, English walnut, European chestnut, cashew), an allergen from a cereal grain (e.g., wheat, corn, barley, oat), an allergen from a fruit (e.g., tomato; apple; banana; rice; avocado; apricot; cherry; plum; peach; pear; strawberry, kiwi, pineapple), an allergen from a vegetable (e.g., celery, potato), an allergen from a seed (e.g., sesame, mustard), an allergen from a fish (e.g., carp, cod, salmon,) an allergen from a crustacean (e.g., shrimp, lobster, crab, oysters), an allergen from a mollusk (e.g., mussels, scallops), an allergen from poultry (e.g., chicken) and an allergen from a dairy product (e.g., egg, milk, cheese). A wide variety of food allergens from these food groups have been characterized and it is contemplated that sequential overlapping epitopes from any such allergen may be readily synthesized and used as described in further detail herein throughout.

A hallmark of allergic disease is the tendency to maintain a persistent IgE response after antigen (allergen) presentation. The IgE specifically recognizes and binds to regions on the allergen. These specific IgE levels may be measured, such as by e.g. ELISA or microarray. The initial exposure to antigens stimulates the production of specific IgE molecules, which bind to high-affinity Fc receptors on the surface of mast cells. Upon reexposure of antigens, the cross-linking of antigens and membrane-bound IgE molecules result in the release of vasoactive mediators, setting off subsequent clinical manifestation. Symptoms of food protein allergy include those commonly associated with IgE-associated reactions, such as angioedema, urticaria, wheezing, rhinitis, vomiting, eczema, and anaphylaxis. Symptoms of IgE-mediated food allergies are similar, regardless of the inciting food allergen.

One type of allergic reaction that requires special attention is anaphylaxis, which is sudden, severe, and potentially fatal, with symptoms that can affect various areas of the body. Anaphylaxis is an acute systemic (multi-system) and severe type I hypersensitivity allergic reaction in humans and other mammals. Anaphylaxis can occur in response to any allergen. Common causes include insect bites or stings, food allergies (peanuts and tree nuts are the most common, though not the only) and drug allergies. Anaphylaxis severity may be scored or graded. This grading system is described in Sampson H A et al. Second symposium on the definition and management of anaphylaxis: Summary report. J Allergy Clin Immunol 2006; 117(2):391-7. A brief summary of an example of a grading system is described below:

| Anaphylaxis Grade | Defined by |
|---|---|
| (1) Mild (skin & subcutaneous tissues, GI, &/or mild respiratory) | Flushing, urticaria, periorbital erythema or angioedema; mild dyspnea, wheeze or upper respiratory symptoms; mild abdominal pain &/or emesis |
| (2) Moderate (mild sxs + features suggesting moderate respiratory, cardiovascular or GI sxs | Marked dysphagia, hoarseness, &/or stridor; SOB, wheezing & retractions; crampy abdominal pain, recurrent vomiting &/or diarrhea; &/or mild dizziness |
| (3) Severe (hypoxia, hypotension, or neurological compromise | Cyanosis or SpO2 ≤92% at any stage, hypotension, confusion, collapse, loss of consciousness; or incontinence |

Anaphylactic shock, the most severe type of anaphylaxis, occurs when an allergic response triggers a quick release of large quantities of immunological mediators (histamines, prostaglandins and leukotrienes) from mast cells, leading to systemic vasodilation (associated with a sudden drop in blood pressure) and edema of bronchial mucosa (resulting in bronchoconstriction and difficulty breathing). The symptoms usually appear very quickly after exposure to the allergen and can include intense itching all over the body, full-body swelling, respiratory distress, and can even lead to life threatening shock. Anaphylactic shock can lead to death in a matter of minutes if left untreated.

A food allergy is an adverse immune response to a food protein. Food allergy is distinct from other adverse responses to food, such as food intolerance (e.g., lactose intolerance), pharmacologic reactions (caffeine tremors, cheese/wine (tyramine) migraine, scombroid (histamine) fish poisoning), and toxin-mediated reactions (bacterial food poisoning, staphylotoxin). Unlike a food allergy, a food intolerance does not involve the immune system. The food protein triggering the allergic response is termed a "food allergen." An example of a food allergen in the present invention is milk (e.g. casein proteins and β-lactoglobulin preset in milk).

The present invention also provides methods for characterizing the binding affinity and/or epitope diversity of antibodies involved in autoimmune diseases, such as e.g., rheumatoid arthritis. In other embodiments antibodies that bind to non-food allergen epitopes involved in IgE-mediated allergic diseases such as e.g., asthma, are characterized.

Cow's milk hypersensitivity is a common disease affecting 2.5% of infants in the first year of life in prospective studies [1], with approximately 60% of these milk disorders due to IgE-mediated mechanisms. The clinical phenotype of milk allergy is characterized by angioedema, urticaria, wheezing, rhinitis, vomiting, diarrhea, eczema, and/or anaphylaxis. The current diagnostic modalities for milk allergy include skin prick testing and measurement of serum milk-specific IgE levels. However, the ultimate diagnosis of milk allergy is determined by Double Blind, Placebo-Controlled Food Challenges (DBPCFC) which is time consuming and involves the risk of anaphylaxis.

As used herein the term "milk IgE profile" refers to the characterization of IgE in a patient sample. The profile includes the total amount of milk-specific IgE in the sample determined by ImmunoCap system (Phadia; Uppsala, Sweden).

A milk allergic subject usually has a higher level of milk-specific IgE compared to non-allergic subject. Individuals with IgE-mediated food allergy often have elevated IgG4 levels as well, but the clinical relevance of this remains to be determined. Some clinicians do measure IgG4, but these levels have never been correlated with clinical symptoms.

Some children who are allergic to cow's milk protein also show concomitant sensitivity to soy-based products. Eight (8) to 14% of infants with symptoms of IgE-associated cow's milk allergy will also react adversely to soy, but reports of anaphylaxis to soy are extremely rare ["Policy Statement: Hypoallergenic Infant Formulas". American Academy of Pediatrics. Aug. 2, 2000]. Many infants with milk and soy allergies can show signs of colic, blood in the stool, mucous in the stool, reflux, rashes and other harmful medical conditions. These conditions are often misdiagnosed as viruses or colic.

Two recent studies suggest that 80% of children will outgrow milk and egg allergy by 15 years of age. As used herein, "to outgrow an allergy" means that the severity of an individual's allergic reaction to an allergen lessens overtime. In most cases, the allergic reaction stops altogether, however, in other cases, the severity of the allergic reaction is reduced to non-dangerous, tolerable levels. Typically, an allergic individual who outgrows an allergy will do so by the age of 18, however, the age at which an individual outgrows his or her allergy can vary depending on the individual.

As used herein, "oral food challenge" or "food challenge" means that a subject ingested a food product containing an allergen (e.g., milk). A "food product" is a food or mixture of food, which can include liquids (e.g., milk) and/or solids (e.g., baked good containing milk) or nuts, such as peanuts. Typical amounts of a food product ingested at the time of food challenge were up to a final dose of 10 gm of food protein. In the present invention, study subjects were characterized based on the results of food challenges as "allergic" (reactive to all forms of milk products), heated cow's milk (HM) tolerant, or as having "outgrown" their milk allergy. Heated cow's milk may be administered to the subjects in the form of cooked food. For example, in the present Examples, the subjects received oral food challenge with muffins, waffles and pizza.

The primary milk proteins involved in cow's milk allergy are α-caseins (αS1- and αS2-caseins), β-casein, κ-casein, and β-lactoglobulin. The amino acid sequences of these proteins (in Bos taurus) are known and have been described: αs1-casein (NP_851372) (SEQ ID NO: 1), αs2-casein (NP_776953.1) (SEQ ID NO: 2), β-casein (P02666) (SEQ ID NO: 3), κ-casein (NP_776719) (SEQ ID NO: 4), and β-lactoglobulin (CAA32835) (SEQ ID NO: 5). See, [25-27].

Non-limiting examples of other food allergens include Peanut: Ara h 1 (L34402), Ara h 2 (AY007229), Ara h 3 (AF093541), Ara h 4 (AF086821), Ara h 5 (AF059616), Ara h 6 (AF092846), Ara h 7 (AF091737), Ara h 8 (AY328088), Ara h 9 (EU159429), Ara h 10 (AY722694), Ara h 11 (DQ097716); Soybean: Gly m 3 (AJ223981 & AJ223982), Gly m 4 (X60043), Gly m 5 (AB008678 & AB008680), Gly m 6 (M36686 & AB113349); Salmon: Sal s 1 (X97824); Egg: Gal d 1 (J00902), Gal d 2 (NP_990483). Common food allergens are well known in the art, and peptide libraries derived from the amino acid sequences of these allergens may be derived, as described by the present invention.

Antibodies

Antibodies are gamma globulin proteins that are found in blood or other bodily fluids of vertebrates, and are used by the immune system to identify and neutralize foreign objects, such as bacteria and viruses. They are also involved in driving allergic responses, such as asthma and food allergies (in particular, IgE and IgG4 in humans). Antibodies, which are produced by B cells, recognize and bind to unique molecular or structural components of antigens. An "antigen" (from antibody-generating) or "immunogen" is a substance that prompts the generation of antibodies and can cause an immune response. For example, in the present invention, casein proteins and β-lactoglobulin are antigens (and also allergens) involved in milk allergy.

The unique part of an antigen recognized by the antibody is termed an "epitope." Epitopes bind with their antibody in a highly specific interaction, called induced fit, which allows antibodies to identify and bind only their unique antigen in the midst of the millions of different molecules that make up an organism. In an immune response, including in allergic responses, a single allergen can contain many different immunogenic epitopes. This means that many different antibodies, each with specificity for a different epitope, can be generated. This is know as a "polyclonal" antibody or humoral immune response.

As used herein, the term "epitope diversity" refers to the number of different immunogenic epitopes on one or more antigens that are recognized by the antibodies generated by an individual's immune response. For example, in the present invention, an individual with serum IgE that binds to more regions of milk peptides than the serum IgE of another individual is said to have an allergic immune response that has greater epitope diversity. Moreover, studies of peanut allergy have suggested that the number of epitopes recognized (i.e., the epitope diversity of an allergic response), rather than recognition of specific epitopes, may be more predictive of clinical features of food allergy [19,20].

An intact antibody comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen.

Following activation with antigen, B cells, which make antibodies, begin to proliferate rapidly. In these rapidly dividing cells, the genes encoding the variable domains of the heavy and light chains of the B cell receptor (and antibodies the B cells produce) undergo a high rate of point mutation, by a process called somatic hypermutation (SHM). SHM results in approximately one nucleotide change per variable gene, per cell division. As a consequence, any daughter B cells will acquire slight amino acid differences in the variable domains of their antibody chains. This serves to increase the diversity of the antibody pool and impacts the antibody's antigen-binding affinity. The "affinity" of an antibody is the strength of binding of a monovalent ligand to a single antigen-binding site on the antibody.

Some point mutations will result in the production of antibodies that have a weaker interaction (low affinity) with their antigen than the original antibody, and some mutations will generate antibodies with a stronger interaction (high affinity). The process of generating antibodies with increased binding affinities is called affinity maturation. The Examples of the present invention demonstrate that the characteristics of both epitope diversity and antibody binding affinity in milk allergic patient, particularly for IgE, are reliably distinguished from the characteristics of individuals who have outgrown their milk allergy or are non-allergic.

There are several different types of antibody heavy chains, and several different kinds of antibodies, which are grouped into different isotypes based on which heavy chain they possess. The five main isotypes of immunoglobulins are IgM, IgD, IgG, IgE, and IgA. In humans, IgG antibodies can be further subdivided into four subclasses (IgG1, IgG2, IgG3, and IgG4), whereas IgA antibodies are found as two subclasses (IgA1 and IgA2). These isotypes perform different roles, and help direct the appropriate immune response for each different type of foreign object they encounter. IgG4 and IgE are involved in a number of different allergic diseases, including milk allergy.

Antibody Binding Assays

In the present invention, methods for determining antibody binding affinity to an allergen in an antibody-containing sample are provided. An "antibody-containing sample" is a sample that contains or is likely to contain an antibody. For example, an antibody-containing sample may be for example serum from a patient. Suitable samples that may be used for characterizing the antibodies present in the sample include, but are not limited to blood or serum, saliva, tissue samples, and breast milk. In certain aspects the binding affinity and epitope diversity of the antibodies in the sample are determined. In some aspects, the affinity and/or epitope diversity is determined using a peptide library immobilized on a solid support. In a specific embodiment of the invention, the affinity and/or epitope diversity is determined using a microarray immunoassay. Examples of other solid support contemplated for use according to the present invention include without limitation, SPOT membrane, Western Blot membrane, ELISA plates, and microbeads (e.g., for analysis in a multiplex assay, such as, e.g., Luminex 100 IS System (BioRad Life Science, Hercules, Calif.) or other cytometric bead array (available, e.g., from BD Biosciences, San Jose, Calif.). Methods using such solid supports for immunoassays, such as detecting antibody binding to an antigen, are well known in the art.

The present invention contemplates the use of any suitable solid support (which may also be referred to as a matrix) known or to be known in the art for the analysis of antibody binding and/or binding affinity according to the present invention.

The methods of the present invention may be applied for the characterization of IgM, IgD, IgE, IgG1, IgG2, IgG3, IgA1 and IgA2.

In a preferred embodiment of the invention, the affinity of IgE antibody is determined using the microarray-based assays in the invention.

In certain aspects, the methods of the present invention have the surprising result of providing a reliable prediction of whether a subject, preferably a human patient, and more preferably a child patient, will outgrow his or her milk allergy. In a specific embodiment, this prediction is made by measuring the affinity of milk-specific IgE antibody in the child's serum using a microarray immunoassay. Further, it is presently discovered that IgE affinity is correlated with clinical features of milk allergy. In certain embodiments, the methods of the invention involve the use of peptide microarray-based assays.

As used herein, a child is a human between the ages of 0 (infant) and 18 years of age. An adult is 18 years of age and older.

As used herein, the term "allergen-specific antibody (e.g., IgE or IgG4) levels" refers to the amount of an antibody in a sample, such as serum, that recognizes a specific allergen (e.g. β-lactoglobulin). Thus, for example, the quantification of β-lactoglobulin-specific IgE levels includes all IgE antibodies (i.e. polyclonal IgE) that recognize any epitope present in β-lactoglobulin.

SPOT membrane-based immunoassays, in which the peptides are synthesized on the nitrocellulose membrane and then incubated with the patient's sera have been used in the past to perform epitope mapping [21]. As used herein "epitope mapping" refers to determining which regions of protein allergens are recognized by antigen-specific antibody involved in allergic disease (e.g., IgE and IgG4). However, synthesis of large numbers of peptides is relatively error prone, time consuming, labor-intensive, and expensive, and has limitations because of the specific chemistry of the method. A large volume of serum is required, and there is also a limitation for the number of targeted peptides. In addition, the SPOT technique is strictly qualitative, with very little statistical analysis possible because of the absence of replicates and small throughput.

The present invention provides microarray-based methods of characterizing antibody epitopes, including epitope mapping, epitope diversity and antibody affinity. Using microarray, it is possible to assay thousands of target peptides in parallel by using small volumes of diluted serum, greatly reducing the biological sample cost of individual assays and allowing for more robust replication and statistical approaches for analysis and epitope determination. Several immunoglobulin subclasses other than IgE can be tested concurrently, allowing simultaneously investigation of potential regulatory responses (e.g., IgG4, IgA, and IgG1) that may influence clinical reactivity.

A protein microarray consists for example of antibodies, proteins, protein fragments, peptides, aptamers or carbohydrate elements that are coated or immobilized ("arrayed") in a grid-like pattern on small surfaces on a solid support. The arrayed molecules are then used to screen and assess patterns of interaction with samples containing distinct proteins or classes of proteins. In certain aspects of the invention, methods using peptide microarray-based assays for characterizing antibody binding to milk allergen epitopes are provided. Characterization of an antibody includes antibody binding affinity and epitope diversity. The present methods are also useful for epitope mapping.

In general, depending upon the method by which peptide microarrays are created, they can be categorized as either the (a) in situ synthesized peptide array, or the (b) spotting peptide array. See, Panicker et al. (2004) Combinatorial Chemistry & High Throughput Screening, 2004, 7, 547-556. As the name implicates, the in situ peptide array is the array on which peptides are synthesized directly on the solid surface. Traditionally, two different techniques are employed, the light-directed parallel chemical synthesis and the SPOT™ synthesis. The spotting array refers to an array of peptides which are presynthesized by any of the combinatorial library methods, then transferred to the solid surface by means of a suitable immobilization technique, typically with the aid of a microarray spotter. Either method is contemplated for use in the present invention, however particulary preferred methods include the use of presynthesized peptides which are spotted on the array slides.

In situ peptide arrays are synthesized using a method called light-directed spatially addressable parallel chemical synthesis, which allows thousands of μm size spots, each containing a unique peptide sequence, to be simultaneously synthesized on a small glass surface. This strategy is made possible by the use of NVOC, a photolabile protecting group to mask the N-terminus of an amino acid, and the glass surface as the solid support during the peptide synthesis. Each deprotection/coupling cycle of the peptide synthesis is precisely controlled by a set of photomasks with predefined configurations which allow for the selective deprotection of the N-terminal amino group of the growing peptide chain, subsequently leading to selective coupling of different amino acids onto different peptides.

In contrast to in situ synthesis methods, spotting peptide array makes use of an automatic microarrayer to spot nanoliter droplets of presynthesized peptide solutions onto a suitably derivatized solid surface, e.g. glass surface. This approach is far more efficient because each peptide needs to be synthesized only once, and multiple copies of the corresponding peptide array may be easily produced by repetitive "printing" using the automatic spotter.

Glass surfaces, such as e.g., epoxy-derivatized glass slides (SuperEpoxy Substrate, Telechem International, Inc.) are used for the microarray assays of the invention. Glass surfaces are ideal for microarray applications because they are physically strong, inexpensive and with low intrinsic fluorescence. They also possess a relatively homogeneous chemical surface which can be easily modified. One of the necessary criteria in a peptide array based biological assay is that, immobilized peptides should preferably adopt an optimally uniform orientation on the glass surface such that they exist in an active state to interact efficiently with incoming molecules. The attachment of peptides/proteins on the surface through noncovalent absorptions (e.g. hydrophobic interactions) typically results in not-so-stable immobilization and leads to random orientation of the biomolecules, thus giving rise to relatively low signal-to-noise ratios in downstream screening assays. A good immobilization method thus should be easily implemented, and at the same time ensure both site-specific and stable immobilization of peptides on the surface.

A variety of methods have been developed for slide derivatization, immobilization of peptides to the surface, and subsequent screenings, etc. [See, e.g., Macbeath, G.; Schreiber, S. L. Science, 2000, 289, 1760-1763; MacBeath, G.; et al. J. Am. Chem. Soc., 1999, 121, 7967-7968; Falsey, J. R.; et al. Bioconj. Chem., 2001, 12, 346-353; Houseman, B. T.; et al. Nat. Biotechnol., 2002, 20, 270-274; Lesaicherre, M. L.; et al. Bioorg. Med. Chem. Lett. 2002, 12, 2079-2083; Lesaicherre, M. L.; et al. Bioorg. Med. Chem. Lett. 2002, 12, 2085-2088; Uttamchandani, M.; et al. Bioorg. Med. Chem. Lett., 2003, 13, 2997-3000; Oliver, C. et al. Bioconj. Chem., 2003, 14, 430-439; Newman, J. R. S.; Keating, A. E. Science, 2003, 300, 2097-2101; Kiyonaka, S.; et al. Nat. Materials, 2004, 3, 58-64; Li, S.; et al. Am. Chem. Soc., 2004, 126, 4088-4089; Cheng, C. W.; et al. Bioorg. Med. Chem. Lett., 2004, 14, 1987-1990; Houseman, B. T.; et al. Langmuir., 2004, 19, 1522-1531; Lesaicherre, M. L.; Lue et al. J. Am. Chem. Soc. 2002, 124, 8768-8769; Lue, R. Y. P.; et al. J. Am. Chem. Soc., 2004, 126, 1055-1062; Salisbury, C. M. et al. J. Am. Chem. Soc. 2002, 124, 14868-14870; Zhu, Q.; et al. Org. Lett., 2003, 5, 1257-1260; and Soellner, M. B.; et al. J. Am. Chem. Soc., 2003, 125, 11790-11791.]

In certain embodiments of the present invention, the microarray slides of the invention are spotted with peptides from a peptide library. As used in the present invention, a peptide library is a collection of peptides of known amino acid sequence that are used to identify antibody epitopes. In some embodiments, the peptide library includes a series of overlapping peptides, wherein the overlapping peptides comprise epitopes. These epitopes can be derived from allergens. As used herein, the term "corresponding to the allergen" refers to the allergen's amino acid sequence. For example, if a peptide of the peptide library corresponds to an allergen, the amino acid sequence of the peptide can be found as part of the amino acids sequence of the allergen (i.e., the peptide is a fragment of the allergen, and can also be said to be "derived from" the allergen).

In certain embodiments, the peptide library is used to identify milk allergen epitopes bound with high affinity by IgE. In a particular embodiment, this identification involves contacting a microarray of a plurality of sequential epitopes from the allergen with serum obtained from the subject and determining the amount of IgE bound to each epitope in the microarray using an anti-IgE antibody. In certain embodiments, the microarray comprises epitopes derived from a plurality of different allergens (e.g. milk allergens); other embodiments contemplate that the microarray is composed of epitopes all derived from the same allergen (e.g., a single protein). The microarray is comprised of different allergens that are derived from the same source (e.g., a specific food, e.g., an array of allergens from milk). In other aspects, the microarray is comprised of different allergens derived from different sources (e.g., from a group of foods).

In specific embodiments of the invention, the peptides are made using overlapping 20-amino-acid sequences. Overlapping peptide sequences overlap by 17 amino acids (3-offset), corresponding to the primary sequences of αs1-casein (61 peptides), αs2-casein (64 peptides), β-casein (64 peptides), and κ-casein (51 peptides), and β-lactoglobulin (49 peptides).

Contemplated for use in the present invention are peptides of any useful length. In general, a peptide is a fragment of a full-length amino acid sequence of a protein, ranging from about 2 amino acid residues to about 100 amino acid residues. In certain aspects, the peptides of the peptide library of the present invention range in sequence length from preferably about 5 to about 50 amino acid residues, more preferably from about 10 to about 40 amino acid residues, and most preferably from about 15 to about 30 amino acid residues. In specific embodiments, the overlapping peptides each comprise an amino acid sequence of from about 10 amino acids in length to about 30 amino acids in length. In further preferred embodiments, each of the overlapping peptides comprises a sequence that overlaps with at least 50% of the sequence of at least one other peptide in the microarray. In other preferred embodiments, the microarray comprises an array of peptides 20 amino acids in length derived from αS1-casein, αS2-casein, κ-casein, β-casein, and β-lactoglobulin, wherein each peptide has a 17 amino acid overlap with at least one other peptide derived from the same allergen.

Any suitable method known in the art for spotting peptides, which may also be referred to as "array elements", for the microarray assays of the invention are contemplated. Array elements may be printed in duplicate (two sets of triplicates) to improve precision and to determine intra-assay variation. In certain aspects of the present invention, peptides were resuspended in DMSO at 2 mg/mL, diluted 1:2 in Protein Printing Buffer (PPB, TeleChem International, Inc., Sunnyvale, Calif.) with 0.02% Sarkosyl to a final concentration of 1 mg/mL and printed to epoxy-derivatized glass slides (SuperEpoxy Substrate, TeleChem International, Inc.) using the NanoPrint™ Microarrayer 60 (TeleChem International, Inc.). The presence of 0.02% Sarkosyl increases the spot size and the peptide spots are more uniform when DMSO and peptide concentrations are increased together. Thus, it is preferable that peptides are printed in 50% DMSO and 0.02% Sarkosyl in PPB. Any suitable microarrayer may be used to print slides.

In certain embodiments of the present invention, PPB alone was used as negative controls and for background normalization, and fluorochrome-labeled bovine serum albumin (BSA) used for the purpose of grid alignment during analysis were included on each slide. For background normalization, the read-out (S) used for each spot, including the replicates for peptides and PPB, was the $\log_2$ transformation of the ratio of the median fluorescent signal of the spot to the median fluorescent signal of the local background. median fluorescent signal of the spot divided by local background and $\log_2$ transformed. A "Z score" was calculated for each array element (spot) using PPB values within the same array (>400 spots/array):

$$Z_i = \frac{S_i - \text{Median}(S_{PPB})}{\text{MAD}(S_{PPB})}$$

By using the above equation, the read-out $S_i$ for the array element was transformed into a Z score ($Z_i$).

A "Z score" is a quantification of antibody binding to a ligand. The Median($S_{PPB}$) and MAD($S_{PPB}$) were the Median and the Median Absolute Deviation (MAD) of all the readouts of PPB spots, respectively. MAD is a robust version of the standard deviation. An final Z value of each peptide element was generated from the Median of Z scores of the six replicate spots. An individual peptide sample was considered positive if its index exceeded 3, meaning that the signal is above the background with p<0.003.

Immunolabeling may be carried out by any method known in the art. In the Examples of the present invention, immunolabeling was performed as previously described with some modifications [12,13]. In this method, slides are blocked with human serum albumin (HSA) to prevent non-specific binding of antibody.

For detection of antibody binding to the peptides immobilized or spotted on the microarray slides, antibody binding is detected with a secondary antibody. For example, if the amount of IgE binding is to be detected, an anti-human IgE secondary antibody may be used. In certain aspects, multiple antibody isotypes may be assayed on the same slide by detecting binding of each isotype using secondary antibodies conjugated to reporter molecules that can be easily distinguished from one another (e.g., can be specifically recognized by different detecting reagents). This secondary antibody may be conjugated to a reporter molecule or to biotin. Non-limiting of examples of reporter molecules include fluorescent molecules, such as e.g., FITC, phycoerythrin (PE), Allophycocyanin (APC) or any other suitable fluorochrome. Biotinylated secondary antibodies may be detected by avidin, or streptavidin conjugated to a reporter molecule, or with an anti-biotin reagent such as anti-Biotin-Dendrimer Oyster 550 (350) (Genisphere, Hatfield, Pa.). FITC labeled secondary antibody may be detected using anti-FITC_Dendrimer_Oyster 650 (350) (Genisphere) in Dendrimer Buffer (Genisphere). Fluorescent dendrimers amplify the signal and lead to ≥100-fold improvement of sensitivity when compared to the direct incorporation of fluorescent label into protein targets.

Microarray data may be analyzed using any suitable software known in the art. Examples include proprietary custom made software (designed by CliniWorks™, Waltham, Mass.) and R programming.

Competition Assay and Data Analysis

In certain aspects, the present invention provides an immunoassay for measuring antibody binding affinity to peptides of a peptide library. In one embodiment, the assay is a microarray-based immunoassay.

In certain embodiments, the assay includes the following sequential steps: (a) obtaining the antibody-containing sample (preferably diluted serum) from the subject; (b) incubating for about 1 to about 24 hours the sample with a peptide library corresponding to said allergen immobilized on a solid support, wherein the peptide library comprises at least one allergen epitope; (c) washing the peptide library; (d) incubating the slides containing the peptide library with a competitor (preferably in the range of 0.1-10 mg/ml), wherein the competitor comprises at least one epitope of the allergen, while incubating another slide (a control) under the same conditions but with no competitor; (e) washing said peptide library; (f) detecting antibody binding to said peptide library in said test group and in said control group; and (g) quantifying and comparing the number of subject antibodies that remain bound to said at least one epitope in said test group and in said control group to determine the affinity of antibody binding to said immobilized allergen epitopes.

The detecting step may be carried out using a secondary antibody, followed by quantification of antibody affinity, as discussed infra. Generally, antibodies of low affinity will disconnect from their peptide ligand mobilized on the solid support and the overall amount of binding will be decreased. On the other hand, antibodies of increasing affinity will dissociate less. This affinity can be calculated using an equation to calculate the Z score, wherein the affinity is high if the Z score is minimally affected (i.e., if the Z score decreases by less than 50%) in binding competition assays of the invention compared to the standard protocol (binding assay with no competitor).

In the binding competition assay of the present invention, a "Z score" represents the strength of antibody binding reaction and the significance above background. To calculate the Z score of immunolabeled microarray slides, an analysis with R version 2.6.0 may be done as follows. Briefly, the readout (S) used for each spot, including the replicates for peptides and protein printing buffer (PPB), is the $\log_2$ transformation of the ratio of the median fluorescent signal of the spot to the median fluorescent signal of the local background. A z ($Z_i$) score is calculated for each array element (spot) by using PPB values within the same array (>400 spots/array): $Z_i = S_i - \text{median}(S_{PPB})/\text{MAD}(S_{PPB})$. By using this equation, the readout Si for the array element was transformed into a Z score ($Z_i$). The median ($S_{PPB}$) and MAD ($S_{PPB}$) were the median and the median absolute deviation (MAD) of all the readouts of PPB spots, respectively. MAD is a robust version of the standard deviation (SD).

In certain embodiments of the invention, an individual peptide sample is considered positive if its z-score exceeded 3, meaning that the signal is significantly above the background (p<0.003). If the Z score of a specific peptide is >3, but none of the 4 adjacent peptides sharing the same epitope with this peptide showing Z score>3, this indicates that the positive signal might come from artifact on the slide and considered as background noise. In order to eliminate non-specific background noise, single positive peptides surrounded by negative binding from 4 adjacent peptides are replaced with the median of itself and the 4 adjacent peptides.

In a specific embodiment of the invention, microarray slides are dotted with milk allergen peptides, and the binding affinity of IgE in the presence of milk allergens (the competitors) is quantified using biotinylated anti-IgE followed by Anti-Biotin-Dendrimer_Oyster 550 (350) (Genisphere, Hatfield, Pa.).

The Wilcoxon test was used to determine statistical differences in reaction levels to each peptide between groups. However, any suitable method for calculating statistical significance may also be used. Methods for calculating statistical significance and for determining the appropriate statistical test are well known in the art.

Figure 5:
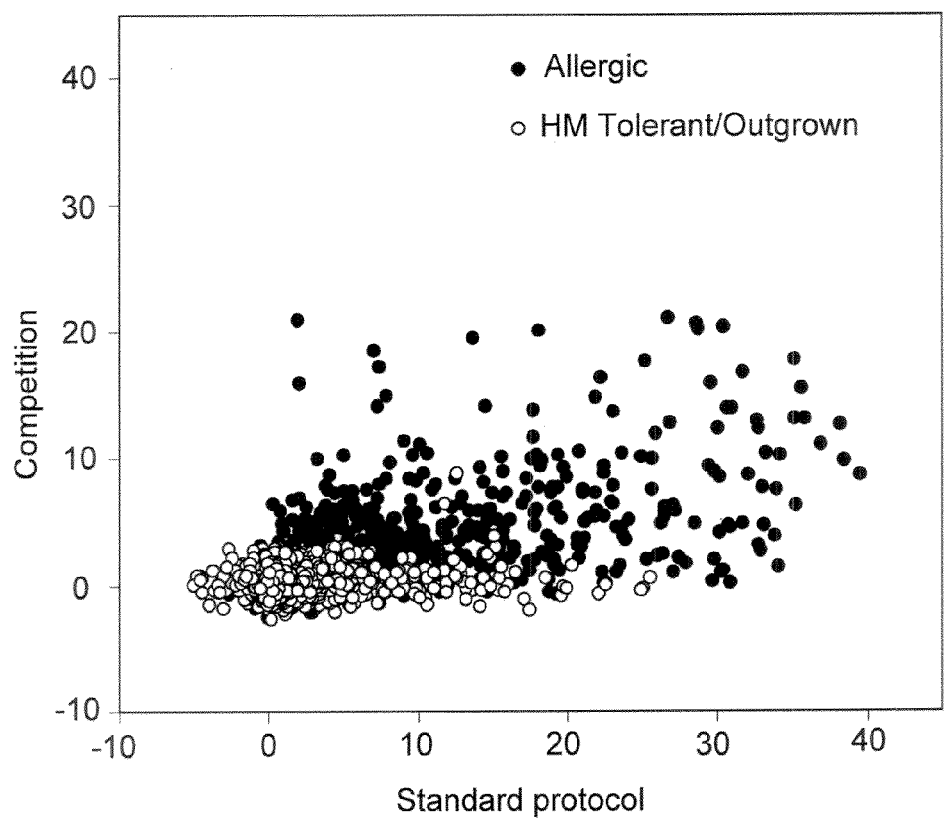
FIG. 5. Scatter plot comparing IgE binding between the standard protocol and the competition assay. Each spot represents IgE binding (represented in Z score) to one milk peptide.

In the present invention, scatter plots are used to graphically represent the ability of a competitor to inhibit binding of an antibody to its epitope (see, e.g., FIG. 5). A scatter plot is a type of mathematical diagram using Cartesian coordinates to display values for two variables for a set of data. A scatter plot can suggest various kinds of correlations between variables with a certain confidence interval. Correlations may be positive (rising), negative (falling), or null (uncorrelated). If the pattern of dots slopes from lower left to upper right, it suggests a positive correlation between the variables being studied. If the pattern of dots slopes from upper left to lower right, it suggests a negative correlation. The data is displayed as a collection of points, each having the value of one variable determining the position on the horizontal axis and the value of the other variable determining the position on the vertical axis. A scatter plot is also called a scatter chart, scatter diagram and scatter graph. In the scatter plots shown in the Figures, increasing binding affinity (Z score) is plotted on the x- and y-axes.

In certain embodiments of the invention, subjects are characterized based on the results of food challenges as "allergic" (reactive to all forms of milk products, heated cow's milk (HM) tolerant (n=16), or "outgrown" (n=8) their milk allergy. The HM-tolerant group all tolerated heated milk in the form of muffins, waffles and pizza, but reacted to regular cow's milk. Blood samples from subjects were obtained at the time of the initial baseline challenge. Eleven non-milk allergic, healthy volunteers served as controls. All research protocols were approved by the Mount Sinai Institutional Review Board, and informed consent was obtained for all subjects.

The food challenge is administered in the fasting state, starting with a dose unlikely to provoke symptoms [25 mg to 100 mg of lyophilized food]. Foods may be masked in various infant formulas for young children, or in elemental formulas, fruit juices [e.g. cranberry, apple, grape], pureed foods or meat patties for older children and adults. In suspected IgE-mediated reactions, the dose generally may be doubled every 15 to 60 minutes and the patient is observed for the development of allergic symptoms. The challenge is discontinued when the patient develops objective signs of an allergic reaction or when the 10 gm dose has been ingested. However, if the patient history describes a more delayed reaction, a longer time interval between doses may be required. Once the patient has tolerated 10 grams of lyophilized food blinded in capsules or liquid [equivalent to about one egg white or one 4 oz glass of milk], clinical reactivity is generally ruled-out. All negative challenges are confirmed by an open feeding under observation to rule-out the rare false-negative challenge.

As shown in the present Examples, the comparison of heated cow's milk (HM) tolerant individuals (i.e., tolerant to heated milk, but not unheated milk) to "allergic" individuals (allergic to all forms of milk) is particularly informative. The analysis of the HM tolerant individuals demonstrates that these individuals have significantly decreased levels of high affinity milk-specific IgE in the serum (i.e., they have fewer milk allergen epitopes bound by high-affinity IgE antibodies), compared to allergic individuals, who have increased numbers of milk allergen epitopes bound by high-affinity IgE.

This discovery makes it possible to identify IgE epitope "hotspots", which are milk allergen epitopes that are frequently recognized by high-affinity IgE antibodies in individuals who are less likely to outgrow their milk allergy. These epitope hotspots are very likely to play an important role in an allergic individual's prognosis, since HM tolerant individuals are more likely to outgrow their milk allergies than allergic individuals [23, 24]. An IgE antibody is characterized to bind with high affinity if its z-score is greater than 3 and its Z score is minimally affected in the binding competition assay of the invention compared to the standard protocol (binding assay with no competitor).

The epitope hotspots of the invention are preferably recognized by antibodies in the milk allergic population at a frequency of about at least 10%-19%, preferably about at least 20%-29%, more preferably about at least 30%-39%, still more preferably about at least 40%-49%, preferably about at least 50%-59%, more preferably about at least 60%-69%, and still more preferably about at least 70%. As used herein, "milk allergic population" refers to all individuals in an analyzed group who are allergic to all forms of milk.

In the present invention, samples are obtained from a patient population in order to make an epitope hotspot profile. Preferably, at least three patient samples are used, more preferably, at least 5 samples, still more preferably, at least 10 samples are used, and most preferably at least 50 or 100 samples are used.

The present invention encompasses in certain embodiments the discovery that IgE epitope hotspots correlate with the clinical phenotypes of milk allergy. It is also discovered that individuals who are more likely to outgrow their milk allergy do not have IgE antibodies that bind these epitope hotspots with high affinity. In certain embodiments, the amino acid sequences of the IgE epitope hotspots may be used to compile a reference profile. A patient sample may be assayed using the methods of the present invention to determine if the patient has IgE antibodies that bind the hotspots in the reference profile with high affinity. If the patient's IgE antibodies bind one or more epitope hotspots in the reference profile, then it is likely that this patient will not outgrow his or her milk allergy. In certain embodiments, a patient is unlikely to outgrow his or her milk allergy if the patient's IgE antibodies bind with high affinity at least 1 IgE epitope hotspot.

Examples of amino acid sequences of IgE epitope hotspots identified by the methods of the present examples include FPEVFGKEKVNELSKDI (SEQ ID NO: 6); QKHIQKED-VPSERYLGYL (SEQ ID NO: 7); LEIVPNSAEERLHS (SEQ ID NO:8); AWYYVPLGTQYTDAPSF (SEQ ID NO: 9); INPSKENLCSTFCKEVV (SEQ ID NO: 10); EVD-DEALEKFDKAL (SEQ ID NO: 11); RFFSDKIAKY-IPIQYVL (SEQ ID NO: 12); DSPEVIESPPEINTVQV (SEQ ID NO: 13); CKEVVRNANEEEYS (SEQ ID NO: 14); and QTPVVVPPFLQPEV (SEQ ID NO: 15). These examples are non-limiting, and the present invention provides methods to reliably identify additional IgE epitope hotspots that are present at a preferred frequency in the milk allergic population. Further, it is to be understood that variants of the above epitope sequences are also contemplated by the invention. For example, the length of the epitopes may be slightly shorter or slightly longer than the above disclosed epitope sequences. Typically, epitopes are at least about 6 amino acids in length. No upper limit is set for the length of an epitope, however epitopes are frequently in the range of 6 to 12 amino acids in length. Further, variants of the epitopes of the invention having amino acid substitutions, additions or deletions are also contemplated for use in the present invention.

It is to be understood that, in addition to IgE, the methods of the present invention may also easily be used to identify epitope hotspots for other antibody isotypes (e.g., IgM, IgG1, IgG2, IgG3, IgG4, IgD, IgA). Further, the methods are useful for identifying epitope hotspots for allergens involved in other allergic diseases. Examples of allergic diseases include other food allergies, such as, e.g., peanut, soy, eggs, tree nuts, fish and wheat.

Figure 6:
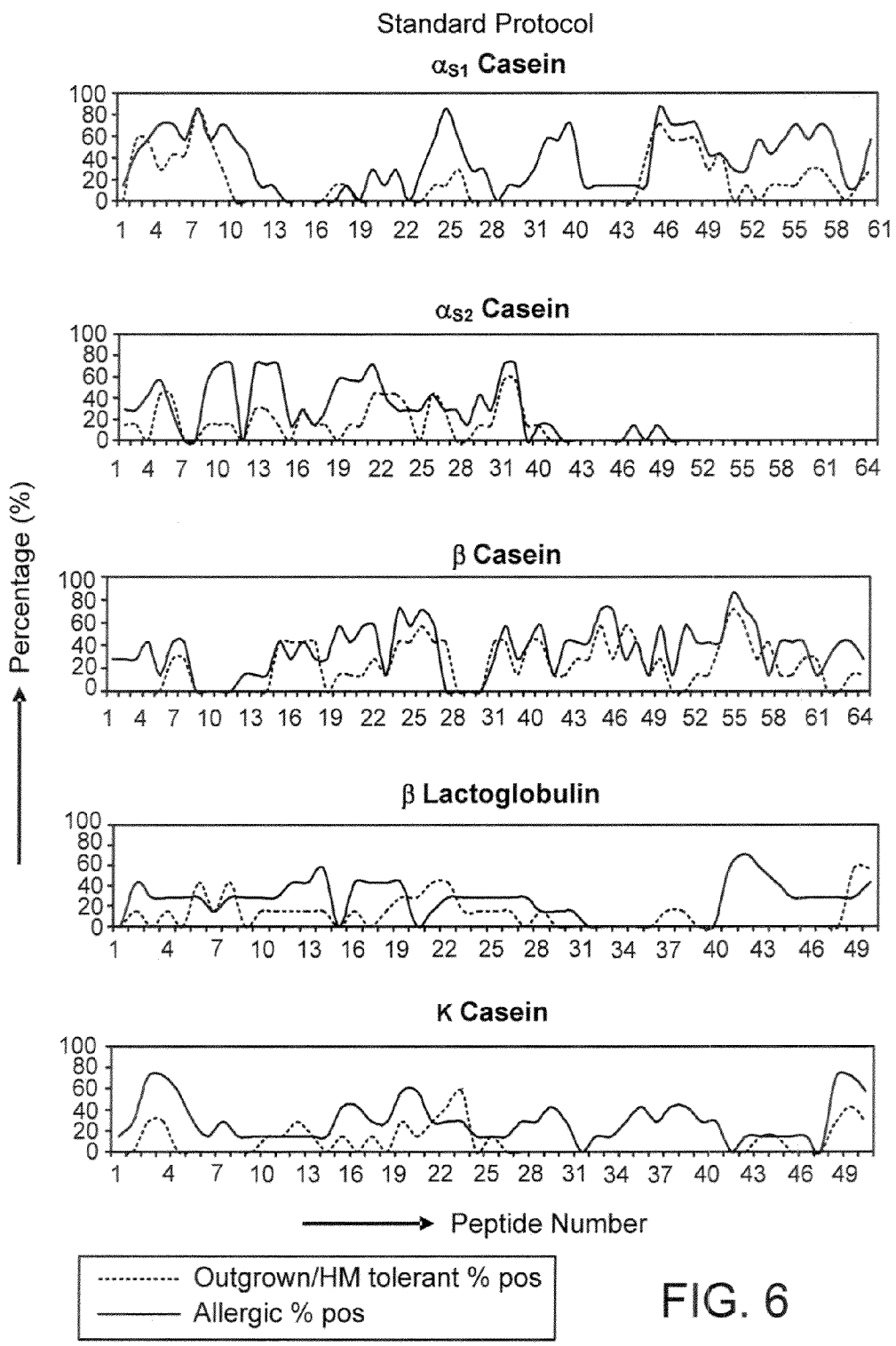
FIG. 6. Comparison of IgE peptide binding frequency between groups using the standard protocol and competition assay. Informative epitopes recognized by >50% of the allergic patients with high affinity IgE antibodies are indicated with the following boxed letters: A (epitope with amino acid sequence corresponding to SEQ ID NO: 14); B (epitope with amino acid sequence corresponding to SEQ ID NO: 15); C (epitope with amino acid sequence corresponding to SEQ ID NO: 11); D (epitope with amino acid sequence corresponding to SEQ ID NO: 12); and E (epitope with amino acid sequence corresponding to SEQ ID NO: 13).
Figure 6:
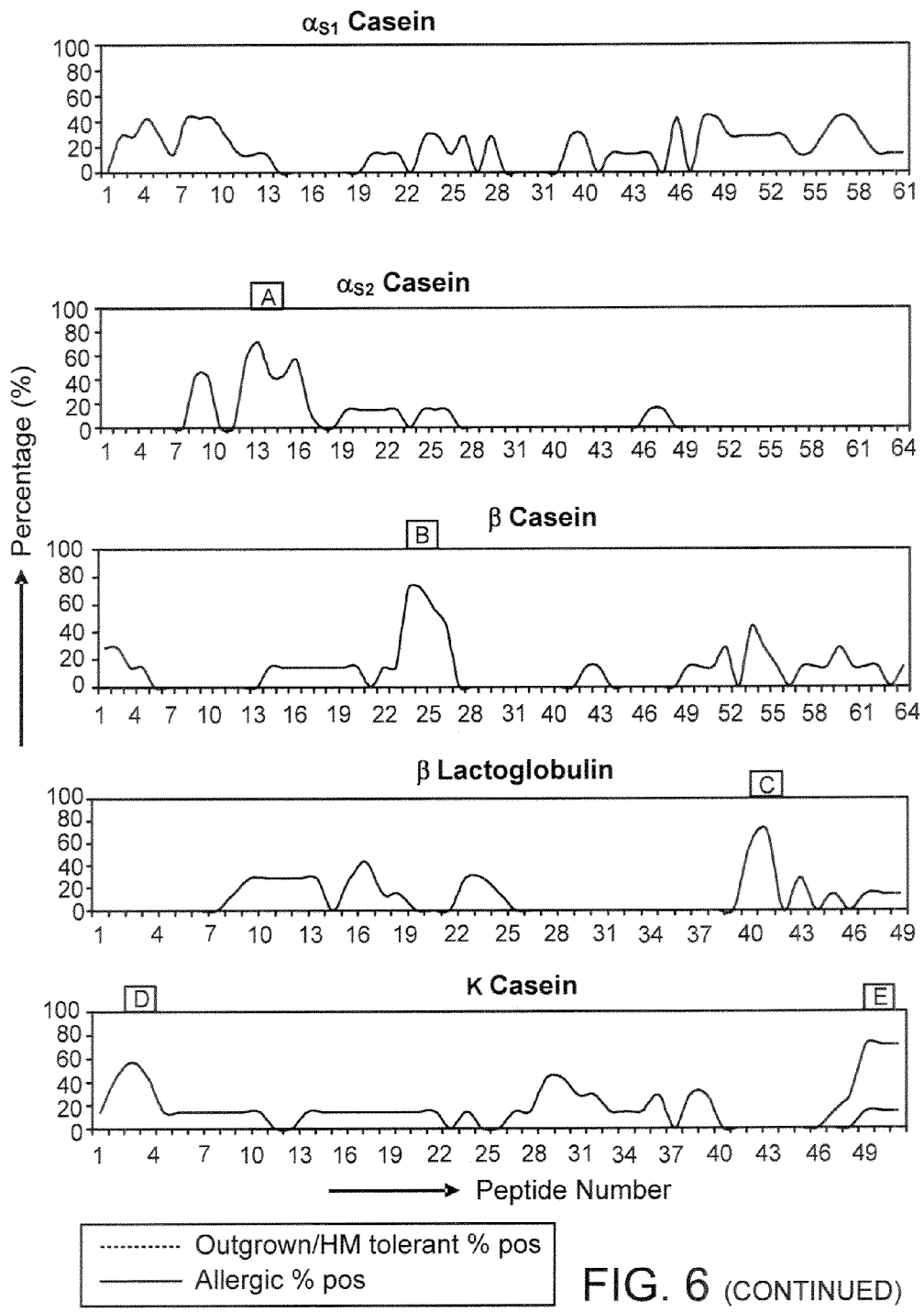

In certain aspects of the present invention, the informative epitopes are identified based on binding of antibodies to one or more peptides of the peptide library. An entire epitope is not always defined by a single peptide sequence in the peptide library. However, since peptide sequences in the library overlap, the epitopes can be deduced based on combining the binding data for all the peptides in the library and mapping the binding. See, e.g., FIGS. 1 and 6. The peptide graphs identify the regions with increased binding by the tested sera. Amino acids of the informative epitopes may be mapped based on the overlapping sequences of the identified peptides. Data presentation may be performed using Microsoft Excel and TIGR Multiexperiment Viewer (TMeV). See, for example, FIG. 3, which shows the sequences of 10 candidate informative epitopes in the casein and β-lactoglobulin proteins.

Figure 2:
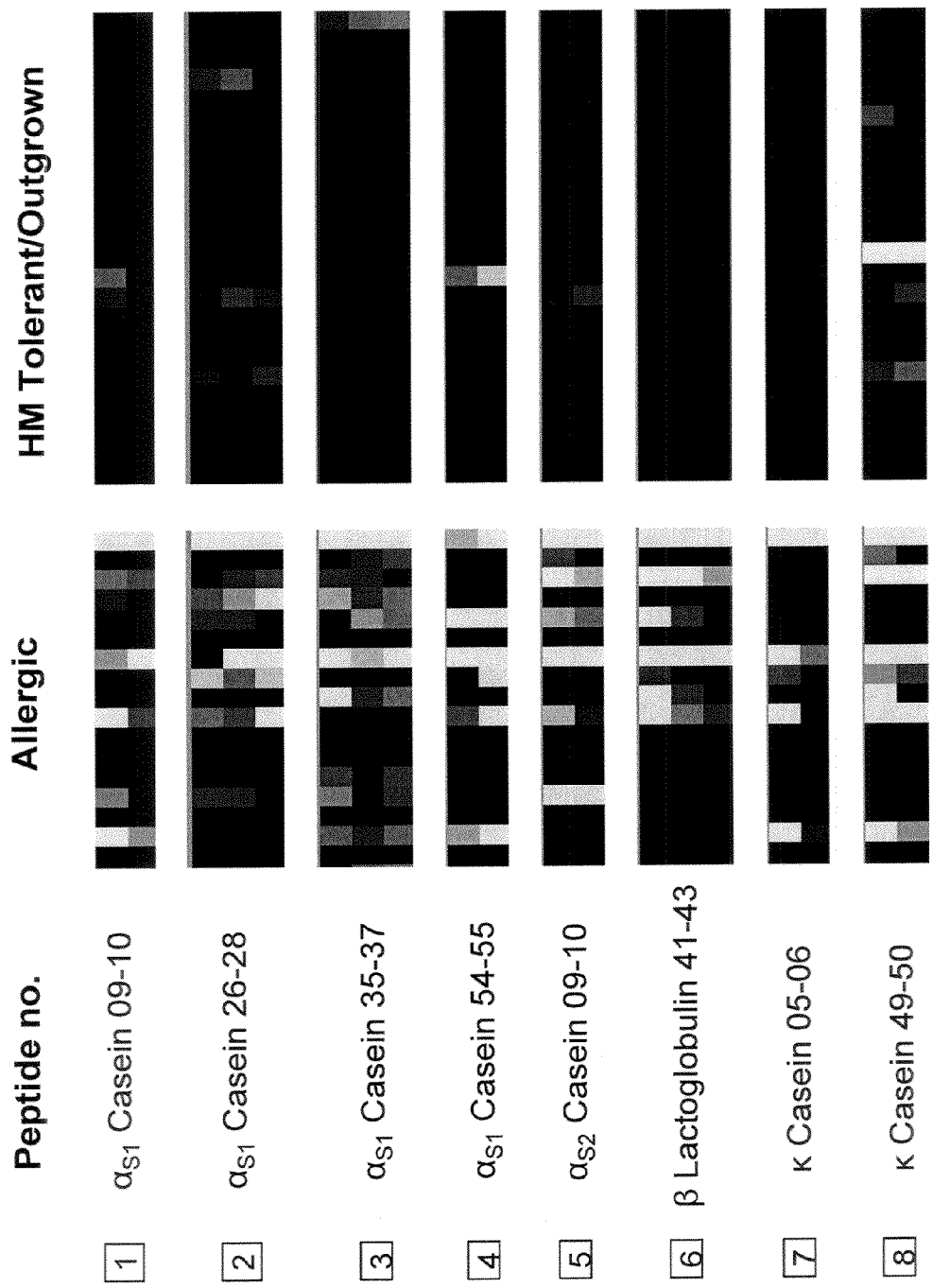
FIG. 2. Heat map of IgE binding to candidates of informative epitopes (labeled nos. 1-8 in FIG. 1) from the allergic patients compared to the HM-tolerant/outgrown patients.

Binding data in the microarray assay is expressed as a "heat map." See, e.g., FIG. 2. A heat map is a graphical representation of data where the values taken by a variable in a two-dimensional map are represented as colors. Darker regions (black) indicate low or no expression of the analyzed parameter (e.g., antibody binding to peptide spotted on the array slide) and colored regions (white, gray) indicate increased expression. In certain aspects of the invention, epitopes are mapped. These are regions that are bound by antibody in the sample being tested. These regions can be identified since the overlapping peptides are spotted sequentially, for example, peptide 1, consisting of amino acid residues 1-20 of a target protein, is spotted (in triplicate), followed by peptide 2, consisting of amino acid residues 4-23, followed by peptide 3, consisting of residues 8-27, etc. If a groups of less than 5 peptides on the slide are positive (bound by antibody), this means that these peptides are in the same region of the protein. If a group of more than 5 adjacent peptides are positive, then multiple epitopes are present in the region, as an epitope typically ranges in size from about 6 to about 12 amino acids.

In certain aspects, the present invention provides methods for diagnosing whether a milk allergic subject is likely to outgrow a milk allergy. In some aspects, this methods includes the steps of quantifying and comparing the number of milk allergen epitopes specifically bound by IgE antibodies present in the sample in the test group and in the control group to determine the affinity of IgE antibody binding to at least one of the milk allergen epitopes. The number of milk allergen epitopes specifically bound by IgE antibodies in the control sample is a measure of the IgE epitope diversity of the sample. Further, the method involves comparing the level of IgE epitope binding affinity to a reference profile of IgE epitope hotspots; and diagnosing whether the subject is likely to outgrow his or her milk allergy. The subject is not likely to outgrow his or her milk allergy if any of the individual's IgE antibodies bind one or more of the IgE epitope hotspots in the reference profile with high affinity.

Competitors

Competitors of the invention are compounds or proteins that interfere with or prevent an antibody from binding to its epitope. Examples of competitors of the invention include but are not limited to full-length casein proteins (e.g., αS1, αS2, κ- and β-caseins) and full-length β-lactoglobulin protein. Also contemplated for use as competitors in the present invention are protein fragments thereof. Mutants and variant forms of the proteins and fragments thereof, including peptides, are also contemplated for use.

In certain embodiments, milk extract may also be used as a competitor. A milk extract is the water-soluble glycoprotein and protein components found in milk. In other embodiments, a mixture of peptides derived from milk allergenic proteins may be used.

Preferred competitors of the invention are those that provide a reduction of antibody binding to its peptide ligand of at least 10%, and more preferably at least 20%, at least 30%, at least 40%, at least 50%, at least 60%, at least 70%, at least 80%, at least 90%, at least 95%, or even at least 99% at a concentration of the competitor, for example, of 1 µg/ml, 10 µg/ml, 100 µg/ml, 500 µg/ml, 1 mg/ml, or 10 mg/ml. Any combination of the above mentioned degrees of percentage competitive inhibition and concentration of competitor may be used to define a competitor of the invention. Further, these competitors may be used alone or in combination of any two or more of the competitors of the invention.

The term "$IC_{50}$" means the concentration of a drug, protein, antibody, small molecule, or other competitor which inhibits an activity or property by 50%, e.g., by reducing the frequency of a condition, such as reducing binding of an antibody to its peptide ligand by 50%.

The preferred temperature range for the competitive inhibition assays of the invention are 4-31° C. In a particularly preferred embodiment, the competitive inhibition step of the microarray immunoassay of the invention is carried out at 16° C. Typically, the competition step of the assays of the invention may be carried out for about 30 minutes to about 18 hours.

Treating or Treatment

"Treating" or "treatment" of a state, disorder or condition includes:

(1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) Inhibiting the state, disorder or condition, i.e., arresting, reducing or delaying the development of the disease or a relapse thereof (in case of maintenance treatment) or at least one clinical or sub-clinical symptom thereof; or (3) Relieving the disease, i.e., causing regression of the state, disorder or condition or at least one of its clinical or sub-clinical symptoms.

The benefit to a subject to be treated is either statistically significant or at least perceptible to the patient or to the physician.

Patient or Subject

"Patient" or "subject" refers to mammals and includes human and veterinary subjects. In certain aspects, the human patients include children, ranging in age from infancy to adulthood. Adulthood is defined as 18 years of age or older.

Immune Response

An "immune response" refers to the development in the host of a cellular and/or antibody-mediated immune response to an antigen. An immune response may also be an allergic immune response. A "humoral immune response" refers to the B cell response, in which plasma B cells secrete antibodies in the blood stream. Allergic immune responses are often, but not necessarily, characterized by elevated serum levels of IgE and/or IgG4, compared to non-allergic (also referred to as "non-atopic") or allergen-tolerant individuals.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Include or Comprise

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

Polymerase Chain Reaction

Polymerase chain reaction (PCR) is a method that allows exponential amplification of short DNA sequences (usually 100 to 600 bases) within a longer double stranded DNA molecule. PCR entails the use of a pair of primers, each about 20 nucleotides in length, that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

Real-Time or Quantitative Polymerase Chain Reaction

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA. The qPCR results may be quantitated using the ΔΔCt method. This method involves calculating a ΔCt between the average target gene Ct and average housekeeping gene Ct for a given target in each treatment group. The ΔΔCt is used to calculate the "n-fold" change in gene expression between groups.

Polymerase

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256: 3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art.

Protein or Polypeptide

The definitions of protein and polypeptide are well-known in the art. The term "protein", as used herein, is synonymous with the term "polypeptide", and is understood to mean a chain of amino acids arranged linearly and joined together by peptide bonds between the carboxyl and amino groups of adjacent amino acid residues.

Amino Acid

The term "amino acid" refers to natural amino acids, unnatural amino acids, and amino acid analogs, all in their D and L stereoisomers if their structures so allow. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Amino acid residues may also be referred to by their 1-letter code, which is well known in the art. Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Variant

The term "variant" may also be used to indicate a modified or altered gene, DNA sequence, enzyme, cell, etc., i.e., any kind of mutant.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., Cell 1987; 50: 667). Such nucleic acid molecules or proteins have sequence homology, as reflected by their sequence similarity, whether in terms of substantial percent similarity or the presence of specific residues or motifs at conserved positions.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein. In the present invention, an antibody may be isolated from a patient or from a patient sample.

Purified

The term "purified" as used herein refers to material that has been isolated under conditions that reduce or eliminate the presence of unrelated materials, i.e. contaminants, including native materials from which the material is obtained. The isolated material is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Enzyme-Linked Immunosorbent Assay (ELISA)

Enzyme-Linked Immunosorbent Assay (ELISA), is a biochemical technique well-known in the art that is used to detect the presence of an antibody or an antigen in a sample. In ELISA, an unknown amount of antigen is affixed to a surface, and then a specific antibody is washed over the surface so that it can bind to the antigen. This antibody is linked to an enzyme (i.e. is a "reporter antibody"), and in the final step a substance is added that the enzyme linked to the reporter antibody can convert to a detectable signal. For example, in the case of fluorescence ELISA, in the presence of light of the appropriate wavelength, any antigen/antibody complexes will fluoresce so that the amount of antigen in the sample can be determined based on the magnitude of the fluorescence.

Performing an ELISA involves at least one antibody with specificity for a particular antigen. The sample with an unknown amount of antigen is immobilized on a solid support (e.g., a polystyrene microtiter plate or beads) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates enabling much higher sensitivity.

Composition

As used herein, the term "composition" indicates a combination of multiple substances into an aggregate mixture.

Kits

In one embodiment, the invention relates to a kit comprising a microarray slide spotted with a peptide library. The peptide library includes at least one milk allergen epitope; and a competitor, wherein the competitor is one or more of the proteins or fragments thereof selected from the group consisting of αS1-casein, αS2-casein, κ-casein, β-casein, and β-lactoglobulin. The peptide library may be the peptide library described in the Examples of the present invention. Modified peptides may also be used. For example, the peptide length may be varied, to be shorter or longer than 20 amino acids. Any peptide length that is suitable for assessing antibody binding characteristics in the microarray-based assays of invention are contemplated for use. In certain embodiments, the kit also includes a detection system (such as, e.g., conjugated anti-human IgE antibody and Dendrimers, as described supra), a positive control (such as, e.g., a serum pool), and blocking reagents/buffers.

Further, directions for use are provided in the kit. In certain embodiments, the direction provide a reference profile of epitope hotspots. In a specific embodiment, a reference profile of IgE epitope hotspots are provided.

In certain aspects, a competitor is provided in a kit. In some embodiments, the competitor may be provided in a solution. In other embodiments, the competitor or inhibitors of the invention are provided in lyophilized form. In a specific embodiment, the solution contains 1% HSA in PBST (blocking buffer). The concentration of competitor may range from about 0.1 to about 10 mg/ml, although higher concentrations are possible. The competitors of the invention may be provided separately or as a part of a kit providing the microarray slides of the invention. Further, directions for use may be provided. In a specific embodiment of the invention, the competitor is any one of the allergens selected from the group consisting of αS1-casein, αS2-casein, κ-casein, β-casein, and β-lactoglobulin. In other embodiments, the competitor is a mixture of any two or more of αS1-casein, αS2-casein, κ-casein, β-casein, and β-lactoglobulin.

In certain aspects, the directions in any of the kits of the invention provide an antibody epitope hotspot reference profile. In a specific embodiment, the reference profile identifies IgE epitopes that indicate a patient is unlikely to outgrow his or her milk allergy, if his or her IgE antibodies bind one or more of the hotspot epitopes with high affinity.

The abbreviations in the specification correspond to units of measure, techniques, properties or compounds as follows: "min" means minutes, "h" means hour(s), "mL" means milliliter(s), "mM" means millimolar, "M" means molar, "μl" means microliter(s); "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Sodium dodecyl sulfate" is abbreviated SDS; and "High Pressure Liquid Chromatography" is abbreviated HPLC. "Ig" means immunoglobulin; "HM" means heated milk, "HSA" means human serum albumin, "PBS-T" means phosphate buffered saline containing 0.05% Tween 20; and "PPB" means protein printing buffer.

EXAMPLES

The present invention is described further below in working examples which are intended to further describe the invention without limiting the scope therein.

Example 1

Materials and Methods

The following describes the materials and methods employed in Examples 2-4.

Patient Sera

Sera previously used for mapping milk protein epitopes by SPOTS membrane technology [3] were used to confirm antigenic areas identified by peptide microarray.

Clinical Study Subjects

To assess the correlation between epitope diversity and affinity and clinical phenotype of milk allergy, 41 subjects were recruited from a larger clinical study on the effects of ingesting heat-denatured milk proteins in milk-allergic individuals. Subjects were characterized based on the results of food challenges as "allergic" (reactive to all forms of milk products, n=17), heated cow's milk (HM) tolerant (n=16), or "outgrown" (n=8) their milk allergy. The HM-tolerant group all tolerated heated milk in the form of muffins, waffles and pizza, but reacted to regular cow's milk. Blood samples from subjects were obtained at the time of the initial baseline challenge. Eleven non-milk allergic, healthy volunteers served as controls. All research protocols were approved by the Mount Sinai Institutional Review Board, and informed consent was obtained for all subjects.

The food challenge is administered in the fasting state, starting with a dose unlikely to provoke symptoms [25 mg to 100 mg of lyophilized food]. Foods may be masked in various infant formulas for young children, or in elemental formulas, fruit juices [e.g. cranberry, apple, grape], pureed foods or meat patties for older children and adults. In suspected IgE-mediated reactions, the dose generally may be doubled every 15 to 60 minutes and the patient is observed for the development of allergic symptoms. The challenge is discontinued when the patient develops objective signs of an allergic reaction or when the 10 gm dose has been ingested. However, if the patient history describes a more delayed reaction, a longer time interval between doses may be required. Once the patient has tolerated 10 grams of lyophilized food blinded in capsules or liquid [equivalent to about one egg white or one 4 oz glass of milk], clinical reactivity is generally ruled-out. All negative challenges are confirmed by an open feeding under observation to rule-out the rare false-negative challenge Allergen-Specific IgE Levels and Skin Test Data Allergen-specific IgE levels were measured by using the ImmunoCAP (Phadia, Portage, Mich.) according to manufacturer's instructions Skin prick tests (SPTs) were performed with a sterile bifurcated needle (Precision Medical Products, Inc, Denver, Pa.), commercial cow's milk extract (Greer Laboratories, Inc, Lenoir, N.C.), and a negative saline and positive histamine control. The size of the skin test response was calculated as a mean of the longest diameter and its longest orthogonal measured at 10 to 15 minutes. To control for the variability of SPTs that might result from the use of different SPT devices and techniques, the ratio of the size of the milk wheal to the histamine wheal was used, presuming that any differences in wheal size caused by the device or technician should be similar and thus not affect the ratio [4].

Microarray

Peptides, Slides, and Printing

A library of peptides was generated. The peptides were made using overlapping 20-amino-acid sequences. Overlapping peptide sequences overlapped by 17 amino acids β-offset), corresponding to the primary sequences of αs1-casein (61 peptides), αs2-casein (64 peptides), β-casein (64 peptides), and κ-casein (51 peptides), and β-lactoglobulin (49 peptides). Peptides were resuspended in DMSO at 2 mg/mL, diluted 1:2 in Protein Printing Buffer (PPB, TeleChem International, Inc., Sunnyvale, Calif.) with 0.02% Sarkosyl to a final concentration of 1 mg/mL and printed to epoxy-derivatized glass slides (SuperEpoxy Substrate, TeleChem International, Inc.) using the NanoPrint™ Microarrayer 60 (TeleChem International, Inc.). PPB alone was used as negative controls and for background normalization, and fluorochrome-labeled bovine serum albumin (BSA) used for the purpose of grid alignment during analysis were included on each slide. All array elements were printed in duplicate (two sets of triplicates) to improve precision and to determine intra-assay variation.

Immunolabeling for Determination of Peptide Binding Frequency and Competition Assays Immunolabeling was performed as previously described with some modifications [12,13]. In brief, the slides were blocked with 400 μl of 1% human serum albumin (HSA) in phosphate-buffered saline containing 0.05% Tween 20 (PBS-T) for 60 minutes at room temperature, followed by incubation with 250 μl of patient serum diluted 1:5 in PBS-T/HSA for 24 hours at 4° C. Slides were then washed with PBS-T and incubated for 24 hours at 4° C. with a cocktail of several monoclonal antibodies including three monoclonal biotinylated anti-human IgE: one from Invitrogen (Carlsbad, Calif., USA) diluted 1:250, one from BD Biosciences Pharmingen (San Jose, Calif., USA) diluted 1:250, and one as a gift from Phadia (Uppsala, Sweden), biotinylated in our laboratory and diluted 1:1000, and one monoclonal anti-human IgG4-FITC (SouthernBiotech, Birmingham, Ala., USA) diluted 1:1000 in PBS-T/HSA. Slides were then incubated for 3 hours at 31° C. with a cocktail of Anti-Biotin-Dendrimer_Oyster 550 (350) (Genisphere, Hatfield, Pa.) and Anti-FITC_Dendrimer_Oyster 650 (350) (Genisphere) in Dendrimer Buffer (Genisphere), both at 0.6 μg/ml with the addition of 0.02 μg/ml of salmon sperm DNA, followed by wash with PBS-T, 15 mM Tris, 0.1×PBS, and 0.05×PBS. Slides were centrifuge dried and scanned using a ScanArray®Gx (PerkinElmer, Waltham, Mass., USA). Images were saved as TIFF format.

Competition Assay

The sera from seven milk allergic subjects and seven HM tolerant/outgrown subjects with binding to multiple milk peptides with the majority of binding having z-scores>5 were selected for a competition assay. The competition assay was performed by immunolabeling the slide as described above with an additional incubation using a mixture of 1 mg/ml of casein, which is a mixture containing αS1-, αS2- β-, and κ-casein (Sigma-Aldrich, St. Louis, Mo.) and 1.6 mg/ml of β-lactoglobulin (Sigma-Aldrich) at 16° C. for 1 hour after serum incubation and before application of the second antibody. Replicate arrays incubated with PBS-T/HSA under the same conditions were used as controls.

Analysis of Peptide Binding Frequency and Statistical Analysis

Fluorescence signal of each spot was digitized with the program ScanArray® Express (Perkin Elmer, Waltham, Mass., USA), exported as comma-delimited text files and transformed to z-score as previously described [10,11]. An index z value of each peptide element was generated from the median of z-scores of the six replicate spots. An individual peptide sample was considered positive if its z-score exceeded 3, meaning that the signal was significantly above the background (p<0.003). In order to eliminate non-specific background noise, single positive peptides with negative binding by 4 adjacent peptides were filtered out by replacement with the median of itself and the 4 adjacent peptides.

The Wilcoxon test was used to determine statistical differences in reaction levels to each peptide between groups. As the peptides overlapped by 17 amino acids, amino acids overlapped by at least two adjacent peptides showing significantly different binding (p<0.05) between groups were considered epitopes. The binding frequency of each group, which is the percentage of patients who had a z-score>3 at each peptide, was also calculated.

For identification of informative epitopes, only areas showing a >30% difference in binding frequency between groups were considered. Then candidates of informative epitopes were identified using peptides within those areas which showed significantly different binding between groups using the Wilcoxon test. Additional informative epitopes were identified based on IgE binding affinity. Amino acids of the informative epitopes were mapped based on the overlapping sequences of the identified peptides. Data presentation was performed using Microsoft Excel and TIGR Multiexperiment Viewer (TMeV).

Example 2

Antigenic Areas Identified by Microarray

Using the serum samples previously used for SPOTS membrane mapping, it was confirmed that allergenic/antigenic areas identified with the peptide microarray correspond well with previously identified regions. Furthermore, microarray was able to detect binding in some areas where it was undetectable on SPOTS, indicating that microarray can be more sensitive than SPOTS membrane technology (data not shown).

Example 3

IgE Diversity Corresponds to Different Phenotypes of Milk Allergy

Characteristics, including age, gender, and milk IgE profile of the patient samples from the clinical study on the natural history of milk allergy are listed on Table 1, below.

TABLE 1

Patient characteristics

|  | Outgrown (n = 8) | Heated milk (HM) tolerant (n = 16) | Allergic (n = 17) |
|---|---|---|---|
| Age (years) | | | |
| Median | 5.8 | 5.7 | 7.3 |
| Mean | 7.9 | 6.6 | 7.7 |
| Range | 2.61-14.69 | 4.84-11.36 | 3.43-14.91 |
| Gender (F/M) | 4/4 | 4/12 | 9/8 |
| Milk IgE (kU/L) | | | |
| Median | 0.9 | 1.8 | 11.6 |
| Mean | 1.4 | 3.23 | 27.7 |
| Range | 0.36-3.23 | 0.35-14.7 | 0.77->100 |

Figure 7:
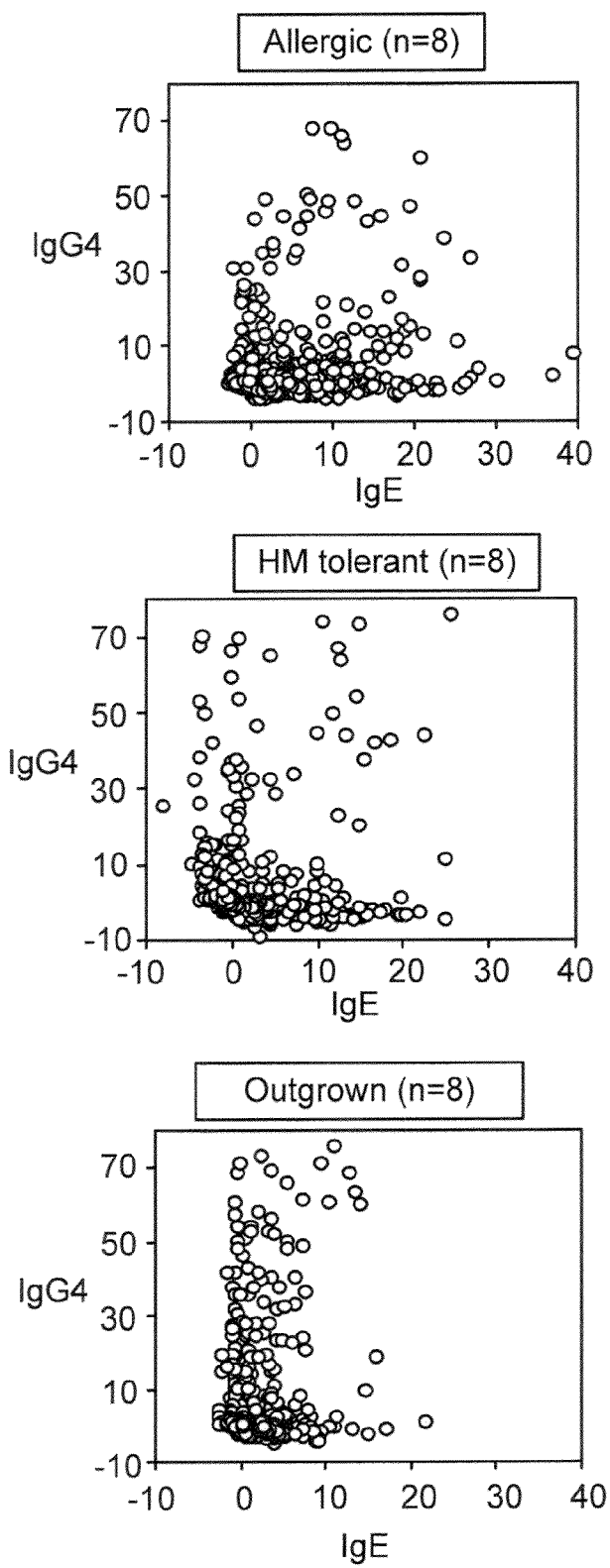
FIG. 7. Scatter plot showing the correlation of IgE and IgG4 bindings of 8 patients from each group. Each spot represents IgE binding (represented in Z score) to one milk peptide.

Sera from patients who have outgrown their milk allergy bound fewer milk peptides with IgE as compared to sera from those with persistent milk allergy (allergic patients) (median IgE peptides bound=3.5 vs 17, p=0.062), but there was no difference in IgG4 binding of peptides. As discussed in Example 1, supra, a peptide was determined to be positive if its z-score was greater than 3. The HM tolerant individuals bound significantly fewer IgE peptides than the allergic group (median IgE peptides bound=3 vs 17, p=0.019), and bound fewer peptides with IgG4 than either those who had outgrown their milk allergy or those who were still allergic (not statistically significant) (Table 2, below, and FIG. 7).

TABLE 2

Number of peptides bound by IgE and IgG$_4$

|  | Outgrown | HM tolerant | Allergic |
|---|---|---|---|
| Number of peptides bound by IgE | | | |
| Mean | 12.3 | 14.6 | 46.6 |
| Median | 3.5 | 3 | 17 |
| Range | 0-66 | 0-103 | 0-186 |
| Number of peptides bound by IgG$_4$ | | | |
| Mean | 19 | 9.1 | 14.7 |
| Median | 9 | 6.5 | 13 |
| Range | 0-93 | 0-40 | 0-56 |

IgE and IgG4 binding frequency to each peptide by each group is shown in FIG. 1. Individuals who were HM tolerant had IgE binding patterns similar to those who had outgrown their milk allergy, but IgG4 binding patterns that were more similar to the allergic group.

IgE binding frequency correlated with severity of symptoms during oral food challenge. Children in the allergic group who had a higher reaction grade during the challenge (anaphylaxis grade 4-5) bound a median of 89.5 IgE peptides whereas children who reacted with anaphylaxis grades 1-2 bound a median of 4.5 IgE peptides (p=0.02). The HM tolerant group generally had milder reactions during their oral food challenges to milk (grades 1-2 only) and bound a median of 3 IgE peptides. There was no correlation between number of IgG4 peptides and severity of allergic reactions during challenge or between number of IgE or IgG4 peptides bound and eliciting dose during challenge.

In order to identify candidates of IgE or IgG4 informative epitopes, HM tolerant and outgrown individuals were combined as one group (HM tolerant/outgrown group, n=24) and compared with the allergic individuals (n=17). Only areas showing a >30% difference in binding frequency between groups were considered. Candidates of informative epitopes were identified as described in the Methods.

Eight areas which fulfilled the criteria listed in the Methods were identified as informative epitopes for IgE (FIGS. 1 and 2). Specifically, only areas showing a >30% difference in binding frequency between groups were considered. The majority were located in αs1-casein, correlating with SPOTS identified epitopes [5-7]. The corresponding IgE epitopes were identified on the protein sequence in FIG. 3. There were no areas with >30% difference between groups for IgG4.

Sera from non-milk allergic subjects were used as controls. Eight (8) of the 11 sera has no detectable IgE binding, 3 subjects had IgE that bound a median of 9 milk peptides. The majority had IgG4 binding to milk peptides (median of 2.5 peptides). Within each clinical group, there was heterogeneity in terms of IgE and IgG4 binding to milk peptides, with each subject having a unique pattern of binding.

Example 4

IgE Affinity Correlates to Different Phenotypes of Milk Allergy

Figure 8:
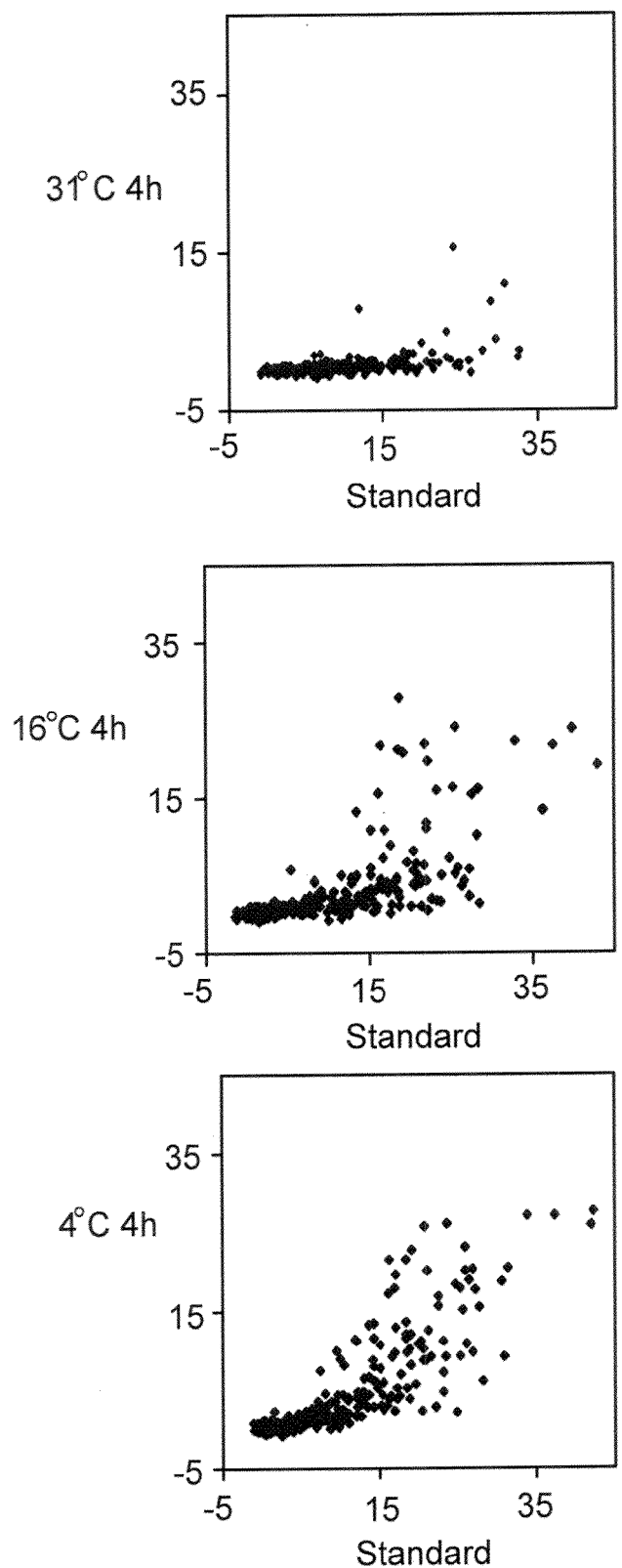
FIG. 8. Effect of temperature. Scatter plot comparing IgE binding between the standard protocol (X-axis) and competition with 2 mg/ml of caseins and 3.2 mg/ml of β-lac at different temperatures (Y-axis) for 4 h. A serum pool of five highly milk allergic individuals was used. Each spot represents IgE binding (represented in Z score) to one milk peptide.

In order to determine the relationship between IgE antibody affinity and clinical allergy phenotype, a competition assay was performed with a subset of patients who had binding to multiple milk epitopes with the majority of binding having z-scores>5 (7 allergic, 5 HM tolerant, and 2 outgrown). The competition conditions, including the concentration of competitor, temperature and length, were first determined using a serum pool of five highly milk allergic individuals (FIG. 8).

Figure 4:
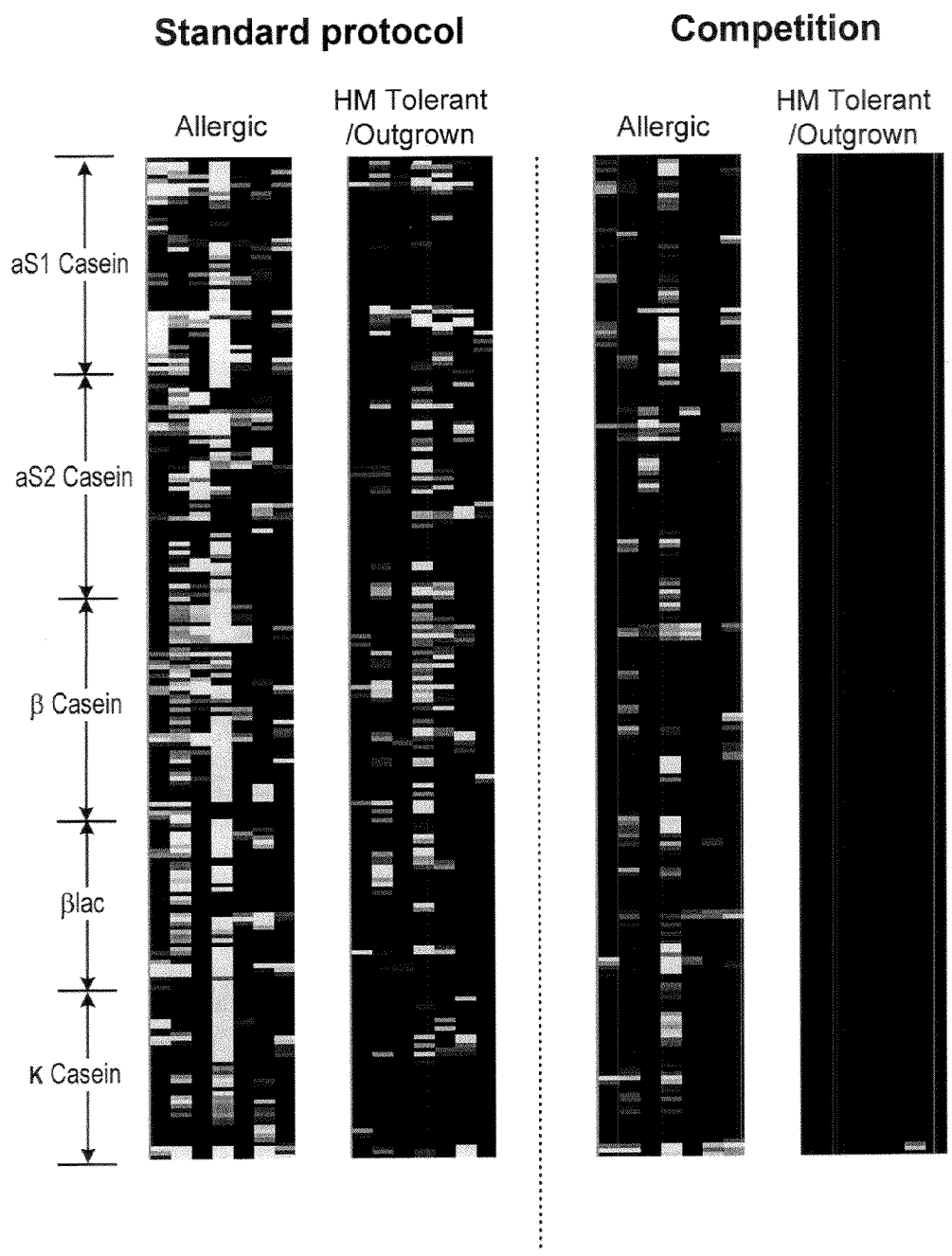
FIG. 4. Heat map showing the effects of competition on 7 allergic and 7 HM-tolerant/outgrown patients.

Compared with the standard protocol (no competition), the competition assay using each of the caseins (αS1-, αS2- β-, or κ-caseins) and β-lactoglobulin virtually eliminated all IgE binding from HM tolerant/outgrown individuals (FIG. 4). No competition effect was observed in arrays incubated with PBS-T/HSA. For patients in the allergic group, IgE binding was affected to a much lesser degree (FIGS. 4 and 5). For allergic patients, IgE antibodies to certain epitopes remained bound following competition, indicating that they were high affinity antibodies. In general, all allergic patients had a mixture of high and low affinity antibodies to different epitopes. There were five epitopes (labeled A-E in FIG. 6) recognized by >50% of the allergic patients whose specific IgE antibodies to these epitopes were of relatively high affinity and not affected or only weakly affected by the competition assay. Three epitopes overlapped with the informative epitopes identified with the standard protocol (C, D, E in FIG. 3). Two additional informative epitopes (A and B) with high antibody affinity are also indicated in FIG. 3.

Example 5

Effect of Competitor Concentration

Figure 9:
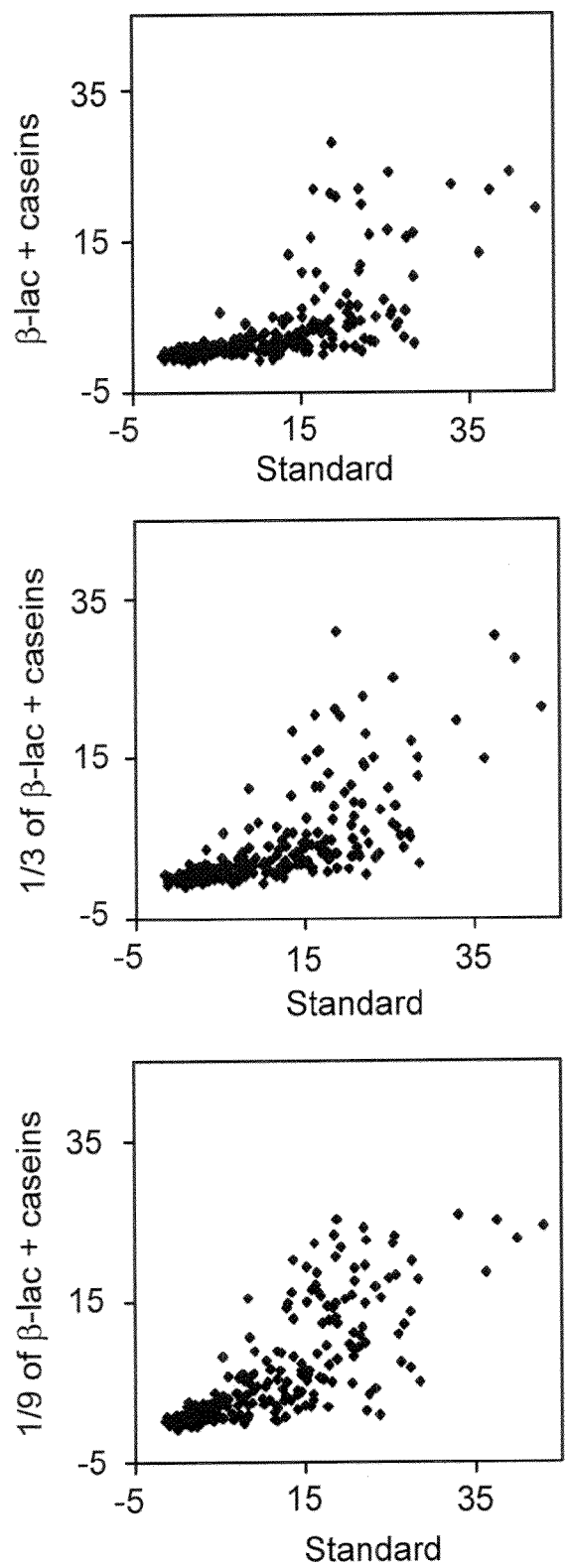
FIG. 9. Effect of competitor concentration. Scatter plot comparing IgE binding of the serum pool between the standard protocol (X-axis) and competition with a 1/3 serial dilution of 2 mg/ml of caseins and 3.2 mg/ml of β-lac (Y-axis) at 16° C. for 4 h.

FIG. 9 shows a scatter plot comparing IgE binding of the serum pool between the standard protocol (X-axis) and competition with a 1/3 serial dilution of 2 mg/ml of caseins and 3.2 mg/ml of β-lac (Y-axis) at 16° C. for 4 h. For competition, 3 slides were incubated at 16° C. for 4 h with 2 mg/ml of caseins and 3.2 mg/ml of β-lac, 0.66 mg/ml of caseins and 1.06 mg/ml of β-lac, and 0.22 mg/ml of caseins and 0.35 mg/ml of β-lac, respectively. 1 slide was processed without competitor.

Example 6

Effect of Competition Time

Figure 10:
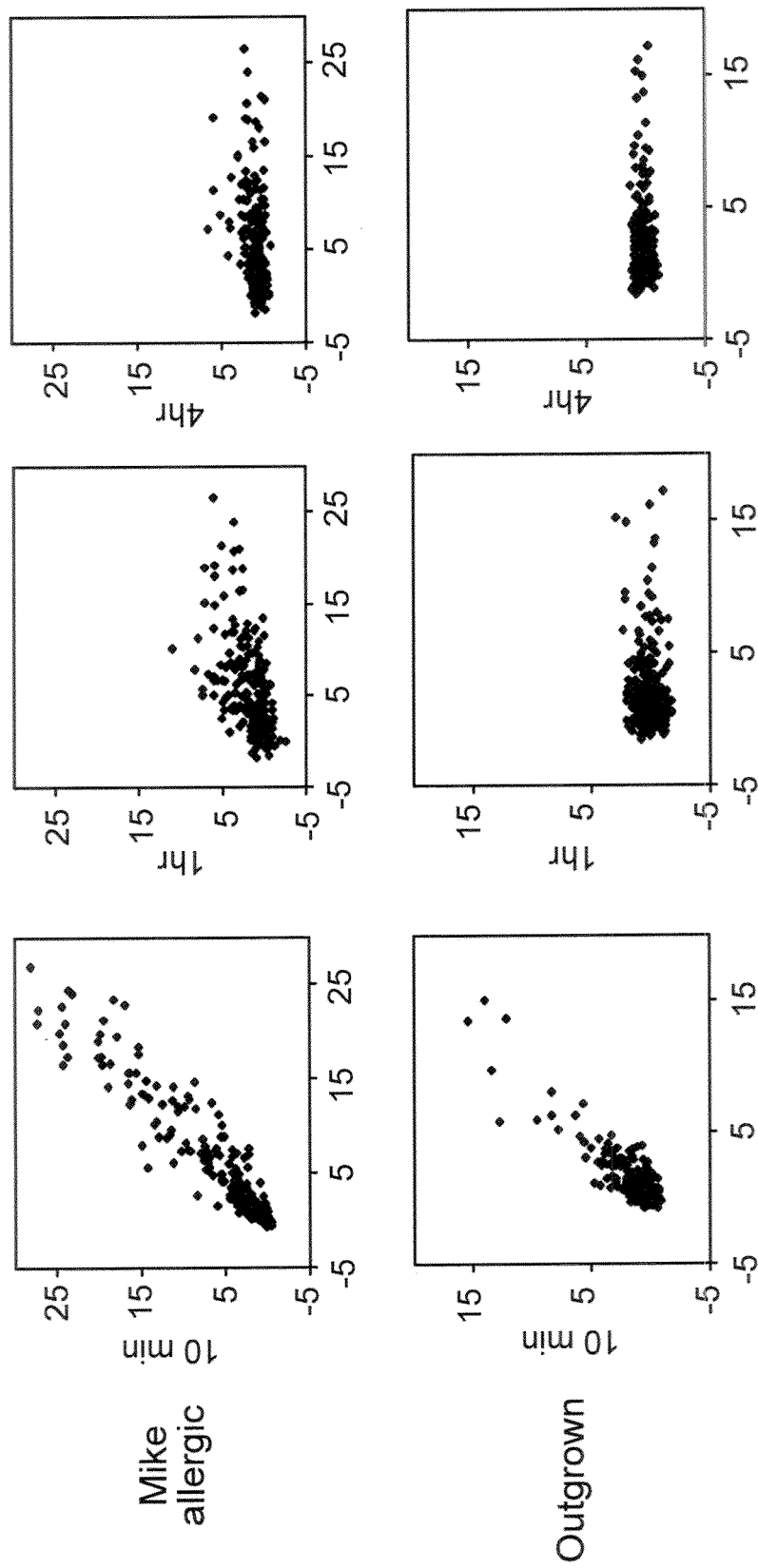
FIG. 10. Effect of competition time. Scatter plot comparing IgE binding of a milk allergic and an outgrown individual between the standard protocol (X-axis) with 1 mg/ml of caseins and 1.6 mg/ml of β-lactoglobulin (Y-axis) at 16° C. for different competition times.

FIG. 10 shows a scatter plot comparing IgE binding of a milk allergic and an outgrown individual between the standard protocol (X-axis) with 1 mg/ml of caseins and 1.6 mg/ml of β-lac (Y-axis) at 16° C. for different competition times. 3 slides were incubated with each serum sample, followed by incubation with competitor (1 mg/ml of caseins and 1.6 mg/ml of β-lac) at 16° C. for various time points. 1 slide was processed without competitor.

Discussion

The aim of this study was to determine whether IgE and IgG4 milk allergen epitope recognition and IgE antibody affinity correlated with different phenotypes of milk allergy. First, it was confirmed that antigenic areas identified with the peptide microarray correspond well with regions previously identified using SPOTS membrane technology, using stored serum from subjects participating in the original study [3]. Next, it was demonstrated that IgE epitope diversity on peptide microarray correlated with clinical phenotypes of milk allergy. Specifically, patients with persistent allergy had increased epitope diversity as compared to those with transient allergy (outgrown). Immunologic studies from the heated milk study show that those who are HM tolerant have a favorable prognosis and are less clinically reactive than those who are unable to tolerated heated milk [4, 14-15]. The microarray data are consistent with these results since IgE from HM tolerant subjects recognized fewer milk allergen peptides than those who were unable to tolerate HM, and were more similar to those who had outgrown their allergy. Furthermore, binding to increased numbers of IgE peptides correlated with severity of allergic reactions during oral food challenge.

IgG4 binding to milk peptides was detected in the majority of patients in all groups. The HM tolerant group tended to have the least amount of IgG4 binding to milk peptides. This was similar to the reported lower quantitative IgG4 levels to casein and β-lactoglobulin in the HM tolerant group [4]. Since strict avoidance is currently the mainstay of treatment, it is possible that IgG4 binding may increase as the HM tolerant group incorporates certain heated milk products in their diets.

Although several IgE epitopes bound by a significantly higher percentage of allergic subjects were identified in the present study, no single informative epitope that reliably distinguished between the different phenotypes of milk allergy could be identified due to the heterogeneity of epitopes recognized by subjects within the different phenotypes. However, an overlap in the number of epitope recognized was also observed.

It is presently discovered that IgE affinity is correlated with clinical features of milk allergy. This is the first time that antibody affinity has been shown to closely reflect clinical characteristics of milk allergy. Milk allergic patients have IgE antibodies that bind to certain areas of milk proteins with high affinity; this binding is not competed off by native milk protein. In contrast, those who have transient allergy (outgrown) or are HM tolerant have low affinity binding that is completely inhibited by native milk protein. These results demonstrate that IgE affinity plays a role in the development of tolerance.

Affinity maturation is an important step in the progressive differentiation of antigen-specific B cells, leading to antibody clones with higher affinity. Thus affinity may be one factor in determining the biological effects of IgE antibodies. However, the role of antibody affinity in allergy has not been well-described. One early report investigated the effect of IgE antibody affinity to Der p 2 on Der p 2-induced histamine release from human basophils and found that the sensitivity of histamine release was closely related to the affinity.[16] Recently, Christensen et al. [17] demonstrated that higher affinity IgE binding to Der p 2 was associated with higher levels of basophil activation.

There is one published report investigating antibody avidity in peanut allergy. Using a thiocyanate ELISA elution assay, the authors found a only weak correlation between IgE and IgG avidity for Ara h 2 and symptom score during oral food challenge [18]. Thiocyanate elution works by non-specifically dissociating antigen-antibody complexes by interfering with non-covalent binding. In contrast, native milk protein was used in the present study as a competitor for IgE binding sites, which is a more relevant indicator of antibody affinity in food allergy. Furthermore, when only antibodies with higher affinity were considered, the overlap observed in the epitope recognition pattern could be eliminated, resulting in a clearer distinction between groups.

Thus, the methods of the present invention provide a useful diagnostic tool that can provide prognostic information regarding outgrowth of and severity of milk allergy based on the epitope diversity and affinity profile. The current diagnostic tools are unable to provide this type of prognostic information, therefore, peptide microarray is a much needed advancement in diagnostics for the field of food allergy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

LITERATURE CITED

1. Sampson H A. Food allergy. Part 1: Immunopathogenesis and clinical disorders. J Allergy Clin Immunol 1999; 103: 717-28.
2. Skripak J M, Matsui E C, Mudd K, Wood R A. The natural history of IgE-mediated cow's milk allergy. J Allergy Clin Immunol. 2007; 120:1172-7.

3. Jarvinen K M, Beyer K, Vila L, Chatchatee P, Busse P J, Sampson H A. B-cell epitopes as a screening instrument for persistent cow's milk allergy. J Allergy Clin Immunol 2002; 110:293-7.
4. Nowak-Wegrzyn A, Bloom K A, Sicherer S H, Shreffler W G, Noone S, Wanich N. et al., Tolerance to extensively heated milk in children with cow's milk allergy. J Allergy Clin Immunol 2008: 122; 342-347.
5. Chatchatee P, Jarvinen K M, Bardina L, Beyer K, Sampson H A. Identification of IgE- and IgG-binding epitopes on alpha(s1)-casein: differences in patients with persistent and transient cow's milk allergy. J Allergy Clin Immunol 2001; 107:379-83.
6. Jarvinen K M, Chatchatee P, Bardina L, Beyer K, Sampson H A. IgE and IgG binding epitopes on alpha-lactalbumin and beta-lactoglobulin in cow's milk allergy. Int Arch Allergy Immunol. 2001; 126:111-8.
7. Chatchatee P, Jarvinen K M, Bardina L, Vila L, Beyer K, Sampson H A. Identification of IgE and IgG binding epitopes on beta- and kappa-casein in cow's milk allergic patients. Clin Exp Allergy. 2001; 31:1256-62.
8. Shreffler W G, Beyer K, Chu T H, Burks A W, Sampson H A. Microarray immunoassay: association of clinical history, in vitro IgE function, and heterogeneity of allergenic peanut epitopes. J Allergy Clin Immunol. 2004; 113:776-82.
9. Flinterman A E, Knol E F, Lencer D A, Bardina L, den Hartog Jager C F, Lin J, et al. Peanut epitopes for IgE and IgG4 in peanut-sensitized children in relation to severity of peanut allergy. J Allergy Clin Immunol. 2008; 121:737-743.
10. Cerecedo I, Zamora J, Shreffler W G, Lin J, Bardina L, Dieguez M C, et al. Mapping of the IgE and IgG4 sequential epitopes of milk allergens with a peptide microarray-based immunoassay. J Allergy Clin Immunol. 2008; 122: 589-94.
11. Pecora V, Nucera E, Schiavino D, Lombardo C, Bardina L, Lin J, et al. Evaluation of specific sequential IgE- and IgG4-binding epitopes, recognized in cow's milk allergic patients during specific oral desensitization, using peptide microarray immunoassay. J Allergy Clin Immunol 2009; 123:S178.
12. Lin J, Bardina L, Shreffler W G, Andreae D A, Ge Y, Wang J, et al. Development of a novel peptide microarray for large scale epitope mapping of food allergens. Allergy Clin Immunol. 2009; 124:315-22.
13. Lin J, Bardina, L, Shreffler W G. Microarrayed allergen molecules for diagnostics of allergy. In: Reineke U, ed. Methods in Molecular Biology-Epitope Mapping Protocols. 2009; 524:259-72.
14. Shreffler W G, Wanich N, Moloney M, Nowak-Wegrzyn A, Sampson H A. Association of allergen-specific regulatory T cells with the onset of clinical tolerance to milk protein. J Allergy Clin Immunol. 2009; 123:43-52.
15. Wanich N, Nowak-Wegrzyn A, Sampson H A, Shreffler W G. Allergen-specific basophil suppression associated with clinical tolerance in patients with milk allergy. J Allergy Clin Immunol. 2009; 123:789-94.
16. Mita H, Yasueda H, Akiyama K. Affinity of IgE antibody to antigen influences allergen-induced histamine release. Clin Exp Allergy. 2000; 30:1583-9.
17. Christensen L H, Holm J, Lund G, Riise E, Lund K. Several distinct properties of the IgE repertoire determine effector cell degranulation in response to allergen challenge. J Allergy Clin Immunol. 2008; 122:298-304.
18. El-Khouly F, Lewis S A, Pons L, Burks A W, Hourihane J O. IgG and IgE avidity characteristics of peanut allergic individuals. Pediatr Allergy Immunol. 2007; 18:607-13.
19. Lewis S A, Grimshaw K E, Warner J O, Hourihane J O. The promiscuity of immunoglobulin E binding to peanut allergens, as determined by Western blotting, correlates with the severity of clinical symptoms. Clin Exp Allergy 2005; 35:767-73.
20. Peeters K A, Koppelman S J, van Hoffen E, van der Tas C W, den Hartog Jager C F, Penninks A H, et al. Does skin prick test reactivity to purified allergens correlate with clinical severity of peanut allergy? Clin Exp Allergy 2007; 37:108-15.
21. Frank R. The SPOT synthesis technique—Synthetic peptide arrays on membrane supports—principles and applications. J Immunol Methods. 2002 September; 267(1):13-26.
22. Sampson H A, Anaphylaxis and Emergency Treatment, PEDIATRICS Vol. 111 No. 6 Jun. 2003, pp. 1601-1608
23. Jarvinen K M, Beyer K, Vila L, Chatchatee P, Busse P J, Sampson H A. B-cell epitopes as a screening instrument for persistent cow's milk allergy. J Allergy Clin Immunol 2002; 110:293-7.
24. Nowak-Wegrzyn A, Bloom K A, Sicherer S H, Shreffler W G, Noone S, Wanich N. et al., Tolerance to extensively heated milk in children with cow's milk allergy. J Allergy Clin Immunol 2008: 122; 342-347.
25. Cocco, R. R., Jarvinen, K. M., Sampson, H. A. and Beyer, K. Mutational analysis of major, sequential IgE-binding epitopes in alpha s1-casein, a major cow's milk allergen JOURNAL J. Allergy Clin. Immunol. 112 (2), 433-437 (2003)
26. Stewart, A. F., Bonsing, J., Beattie, C. W., Shah, F., Willis, I. M. and Mackinlay, A. G. Complete nucleotide sequences of bovine alpha S2- and beta-casein cDNAs: comparisons with related sequences in other species JOURNAL Mol. Biol. Evol. 4 (3), 231-241 (1987)
27. Hallen, E., Wedholm, A., Andren, A. and Lunden, A. Effect of beta-casein, kappa-casein and beta-lactoglobulin genotypes on concentration of milk protein variants JOURNAL J. Anim. Breed. Genet. 125 (2), 119-129 (2008)

What is claimed is:

1. A method for diagnosing whether a cow's milk allergic child is likely to outgrow a cow's milk allergy, which method comprises:
   (a) incubating an antibody-containing sample obtained from the child with a peptide library immobilized on a solid support to form an incubation mixture, wherein the peptide library comprises at least one epitope consisting of an amino acid sequence selected from the group consisting of FPEVFGKEKVNELSKDI (SEQ ID NO: 6); QKHIQKEDVPSERYLGYL (SEQ ID NO: 7); LEIVPNSAEERLHS (SEQ ID NO:8); AWYYVPLGTQYT-DAPSF (SEQ ID NO: 9); INPSKENLCSTFCKEVV (SEQ ID NO: 10); EVDDEALEKFDKAL (SEQ ID NO: 11); RFFSDKIAKYIPIQYVL (SEQ ID NO: 12); DSPEVIESPPEINTVQV (SEQ ID NO: 13); CKEVVRNANEEEYS (SEQ ID NO: 14); and QTPVVVPPFLQPEV (SEQ ID NO: 15);
   (b) incubating a first portion of the incubation mixture with a competitor (competition protocol), wherein the competitor comprises the amino acid sequence of the at least one epitope set forth in (a), and incubating a second portion of the incubation mixture under the same conditions but in the absence of the competitor (standard protocol);

(c) detecting IgE antibody binding to the at least one epitope in the peptide library in the competition protocol and in the standard protocol;

(d) determining the binding affinity of the IgE antibody binding to the at least one epitope in the peptide library detected in step (c); and (e) diagnosing the child as not likely to outgrow the cow's milk allergy if the sample comprises an IgE antibody that binds to the at least one epitope in the peptide library with high affinity; or diagnosing the child as likely to outgrow the cow's milk allergy if the sample does not comprise an IgE antibody that binds to the at least one epitope in the peptide library with high affinity.

2. The method of claim 1, wherein the peptide library further comprises a series of overlapping peptides that are fragments of at least one cow's milk allergen selected from the group consisting of $\alpha_{S1}$-casein, $\alpha_{S2}$-casein, κ-casein, β-casein, and β-lactoglobulin.

3. The method of claim 2, wherein:
the at least one cow's milk allergen is αS1-casein and the competitor further comprises αS1-casein; or
the at least one cow's milk allergen is αS2-casein and the competitor further comprises αS2-casein; or
the at least one cow's milk allergen is K casein and the competitor further comprises κ casein; or
the at least one cow's milk allergen is β-casein and the competitor further comprises β-casein; or
the at least one cow's milk allergen is β-lactoglobulin and the competitor further comprises β-lactoglobulin.

4. The method of claim 1, wherein the incubation step (a) is carried out at a temperature ranging from about 0 to about 15 degrees Celsius.

5. The method of claim 1, wherein the incubation step (a) is carried out at a temperature of 4 degrees Celsius.

6. The method of claim 1, wherein the incubation in step (a) is carried out for at least 5 minutes.

7. The method of claim 1, wherein the incubation in step (a) is carried out for at least 1 hour.

8. The method of claim 1, wherein the incubation in step (a) is carried out for at least 24 hours.

9. The method of claim 1, wherein the incubation step (b) is carried out at a temperature in the range of about 4 to about 50 degrees Celsius.

10. The method of claim 1, wherein the incubation step (b) is carried out at a temperature of 16 degrees Celsius.

11. The method of claim 1, wherein the detecting in step (c) comprises:
(i) incubating the first and second portions, corresponding to the competition protocol and the standard protocol, respectively, with a secondary anti-IgE antibody, to form two secondary antibody incubation mixtures;
(ii) incubating each secondary antibody incubation mixture with a fluorescently-labeled dendrimer to form two dendrimer incubation mixtures, wherein the dendrimer is capable of specifically binding the secondary anti-IgE antibody; and
(iii) detecting any dendrimer bound to the secondary antibody in each dendrimer incubation mixture.

12. The method of claim 11, wherein the secondary antibody is incubated with the first and second portions at about 4 degrees Celsius.

13. The method of claim 11, wherein the dendrimer is incubated with the first and second portions at about 31 degrees Celsius.

14. The method of claim 1, wherein the binding affinities are determined in step (d) by calculating a Z score of antibody binding to the at least one epitope in the peptide library in the competition protocol and the standard protocol and comparing the Z score determined in each, wherein the antibody is a high affinity antibody if the Z score is greater than three (3) and the difference between the Z score in the competition protocol and the standard protocol is less than about 50 percent.

15. The method of claim 2, wherein each of the overlapping peptides has a length in the range of 5 to 50 amino acid residues.

16. The method of claim 1, wherein the at least one epitope consists of the amino acid sequence FPEVFGKEKVNELSKDI (SEQ ID NO: 6).

17. The method of claim 1, wherein the at least one epitope consists of the amino acid sequence QKHIQKEDVPSERYLGYL (SEQ ID NO: 7).

18. The method of claim 1, wherein the at least one epitope consists of the amino acid sequence LEIVPNSAEERLHS (SEQ ID NO:8).

19. The method of claim 1, wherein the at least one epitope consists of the amino acid sequence AWYYVPLGTQYTDAPSF (SEQ ID NO: 9).

20. The method of claim 1, wherein the at least one epitope consists of the amino acid sequence INPSKENLCSTFCKEVV (SEQ ID NO: 10).

21. The method of claim 1, wherein the at least one epitope consists of the amino acid sequence EVDDEALEKFDKAL (SEQ ID NO: 11).

22. The method of claim 1, wherein the at least one epitope consists of the amino acid sequence RFFSDKIAKYIPIQYVL (SEQ ID NO: 12).

23. The method of claim 1, wherein the at least one epitope consists of the amino acid sequence DSPEVIESPPEINTVQV (SEQ ID NO: 13).

24. The method of claim 1, wherein the at least one epitope consists of the amino acid sequence CKEVVRNANEEEYS (SEQ ID NO: 14).

25. The method of claim 1, wherein the at least one epitope consists of the amino acid sequence QTPVVVPPFLQPEV (SEQ ID NO: 15).

* * * * *

SEQUENCE LISTING

```
<160> NUMBER OF SEQ ID NOS: 15

<210> SEQ ID NO 1
<211> LENGTH: 214
<212> TYPE: PRT
<213> ORGANISM: Bos taurus
<300> PUBLICATION INFORMATION:
<308> DATABASE ACCESSION NUMBER: Genbank Accession Number: NP_851372

<400> SEQUENCE: 1
```

```
Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
            35                  40                  45

Lys Glu Lys Val Asn Glu Leu Ser Lys Asp Ile Gly Ser Glu Ser Thr
50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
    130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 2
<211> LENGTH: 222
<212> TYPE: PRT
<213> ORGANISM: Bos taurus
<300> PUBLICATION INFORMATION:
<308> DATABASE ACCESSION NUMBER: Genbank Accession Number: NP_776953.1

<400> SEQUENCE: 2

Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
                20                  25                  30

Glu Thr Tyr Lys Gln Glu Lys Asn Met Ala Ile Asn Pro Ser Lys Glu
            35                  40                  45

Asn Leu Cys Ser Thr Phe Cys Lys Glu Val Val Arg Asn Ala Asn Glu
        50                  55                  60

Glu Glu Tyr Ser Ile Gly Ser Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
    130                 135                 140
```

```
Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Lys Asn Arg Leu
            165                 170                 175

Asn Phe Leu Lys Lys Ile Ser Gln Arg Tyr Gln Lys Phe Ala Leu Pro
        180                 185                 190

Gln Tyr Leu Lys Thr Val Tyr Gln His Gln Lys Ala Met Lys Pro Trp
            195                 200                 205

Ile Gln Pro Lys Thr Lys Val Ile Pro Tyr Val Arg Tyr Leu
210                 215                 220
```

<210> SEQ ID NO 3
<211> LENGTH: 224
<212> TYPE: PRT
<213> ORGANISM: Bos taurus
<300> PUBLICATION INFORMATION:
<308> DATABASE ACCESSION NUMBER: Genbank Accession Number: P02666

<400> SEQUENCE: 3

```
Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
    210                 215                 220
```

<210> SEQ ID NO 4
<211> LENGTH: 190
<212> TYPE: PRT
<213> ORGANISM: Bos taurus
<300> PUBLICATION INFORMATION:
<308> DATABASE ACCESSION NUMBER: Genbank Accession Number: NP_776719

<400> SEQUENCE: 4

```
Met Met Lys Ser Phe Phe Leu Val Val Thr Ile Leu Ala Leu Thr Leu
```

```
                1               5                  10                 15
            Pro Phe Leu Gly Ala Gln Glu Gln Asn Gln Glu Gln Pro Ile Arg Cys
                            20                  25                  30

Glu Lys Asp Glu Arg Phe Phe Ser Asp Lys Ile Ala Lys Tyr Ile Pro
                            35                  40                  45

Ile Gln Tyr Val Leu Ser Arg Tyr Pro Ser Tyr Gly Leu Asn Tyr Tyr
                            50                  55                  60

Gln Gln Lys Pro Val Ala Leu Ile Asn Asn Gln Phe Leu Pro Tyr Pro
            65                  70                  75                  80

Tyr Tyr Ala Lys Pro Ala Ala Val Arg Ser Pro Ala Gln Ile Leu Gln
                            85                  90                  95

Trp Gln Val Leu Ser Asn Thr Val Pro Ala Lys Ser Cys Gln Ala Gln
                            100                 105                 110

Pro Thr Thr Met Ala Arg His Pro His Pro His Leu Ser Phe Met Ala
                            115                 120                 125

Ile Pro Pro Lys Lys Asn Gln Asp Lys Thr Glu Ile Pro Thr Ile Asn
                            130                 135                 140

Thr Ile Ala Ser Gly Glu Pro Thr Ser Thr Pro Thr Thr Glu Ala Val
            145                 150                 155                 160

Glu Ser Thr Val Ala Thr Leu Glu Asp Ser Pro Glu Val Ile Glu Ser
                            165                 170                 175

Pro Pro Glu Ile Asn Thr Val Gln Val Thr Ser Thr Ala Val
                            180                 185                 190

<210> SEQ ID NO 5
            <211> LENGTH: 178
            <212> TYPE: PRT
            <213> ORGANISM: Bos taurus
            <300> PUBLICATION INFORMATION:
            <308> DATABASE ACCESSION NUMBER: Genbank Accession Number: CAA32835

<400> SEQUENCE: 5

Met Lys Cys Leu Leu Leu Ala Leu Ala Leu Thr Cys Gly Ala Gln Ala
              1               5                  10                  15

Leu Ile Val Thr Gln Thr Met Lys Gly Leu Asp Ile Gln Lys Val Ala
                            20                  25                  30

Gly Thr Trp Tyr Ser Leu Ala Met Ala Ala Ser Asp Ile Ser Leu Leu
                            35                  40                  45

Asp Ala Gln Ser Ala Pro Leu Arg Val Tyr Val Glu Glu Leu Lys Pro
                            50                  55                  60

Thr Pro Glu Gly Asp Leu Glu Ile Leu Leu Gln Lys Trp Glu Asn Asp
            65                  70                  75                  80

Glu Cys Ala Gln Lys Lys Ile Ile Ala Glu Lys Thr Lys Ile Pro Ala
                            85                  90                  95

Val Phe Lys Ile Asp Ala Leu Asn Glu Asn Lys Val Leu Val Leu Asp
                            100                 105                 110

Thr Asp Tyr Lys Lys Tyr Leu Leu Val Cys Met Glu Asn Ser Ala Glu
                            115                 120                 125

Pro Glu Gln Ser Leu Val Cys Gln Cys Leu Val Arg Thr Pro Glu Val
                            130                 135                 140

Asp Asp Glu Ala Leu Glu Lys Phe Asp Lys Ala Leu Lys Ala Leu Pro
            145                 150                 155                 160

Met His Ile Arg Leu Ser Phe Asn Pro Thr Gln Leu Glu Glu Gln Cys
                            165                 170                 175

His Ile
```

<210> SEQ ID NO 6
<211> LENGTH: 17
<212> TYPE: PRT
<213> ORGANISM: Artificial Sequence
<220> FEATURE:
<223> OTHER INFORMATION: Antibody Epitopes on Milk Allergens

<400> SEQUENCE: 6

Phe Pro Glu Val Phe Gly Lys Glu Lys Val Asn Glu Leu Ser Lys Asp
 1               5                  10                  15

Ile

<210> SEQ ID NO 7
<211> LENGTH: 18
<212> TYPE: PRT
<213> ORGANISM: Artificial Sequence
<220> FEATURE:
<223> OTHER INFORMATION: Antibody Epitopes on Milk Allergens

<400> SEQUENCE: 7

Gln Lys His Ile Gln Lys Glu Asp Val Pro Ser Glu Arg Tyr Leu Gly
 1               5                  10                  15

Tyr Leu

<210> SEQ ID NO 8
<211> LENGTH: 14
<212> TYPE: PRT
<213> ORGANISM: Artificial Sequence
<220> FEATURE:
<223> OTHER INFORMATION: Antibody Epitopes on Milk Allergens

<400> SEQUENCE: 8

Leu Glu Ile Val Pro Asn Ser Ala Glu Glu Arg Leu His Ser
 1               5                  10

<210> SEQ ID NO 9
<211> LENGTH: 17
<212> TYPE: PRT
<213> ORGANISM: Artificial Sequence
<220> FEATURE:
<223> OTHER INFORMATION: Antibody Epitopes on Milk Allergens

<400> SEQUENCE: 9

Ala Trp Tyr Tyr Val Pro Leu Gly Thr Gln Tyr Thr Asp Ala Pro Ser
 1               5                  10                  15

Phe

<210> SEQ ID NO 10
<211> LENGTH: 17
<212> TYPE: PRT
<213> ORGANISM: Artificial Sequence
<220> FEATURE:
<223> OTHER INFORMATION: Antibody Epitopes on Milk Allergens

<400> SEQUENCE: 10

Ile Asn Pro Ser Lys Glu Asn Leu Cys Ser Thr Phe Cys Lys Glu Val
 1               5                  10                  15

Val

<210> SEQ ID NO 11
<211> LENGTH: 14
<212> TYPE: PRT
<213> ORGANISM: Artificial Sequence

```
<220> FEATURE:
<223> OTHER INFORMATION: Antibody Epitopes on Milk Allergens

<400> SEQUENCE: 11

Glu Val Asp Asp Glu Ala Leu Glu Lys Phe Asp Lys Ala Leu
 1               5                  10

<210> SEQ ID NO 12
<211> LENGTH: 17
<212> TYPE: PRT
<213> ORGANISM: Artificial Sequence
<220> FEATURE:
<223> OTHER INFORMATION: Antibody Epitopes on Milk Allergens

<400> SEQUENCE: 12

Arg Phe Phe Ser Asp Lys Ile Ala Lys Tyr Ile Pro Ile Gln Tyr Val
 1               5                  10                  15
Leu

<210> SEQ ID NO 13
<211> LENGTH: 17
<212> TYPE: PRT
<213> ORGANISM: Artificial Sequence
<220> FEATURE:
<223> OTHER INFORMATION: Antibody Epitopes on Milk Allergens

<400> SEQUENCE: 13

Asp Ser Pro Glu Val Ile Glu Ser Pro Pro Glu Ile Asn Thr Val Gln
 1               5                  10                  15
Val

<210> SEQ ID NO 14
<211> LENGTH: 14
<212> TYPE: PRT
<213> ORGANISM: Artificial Sequence
<220> FEATURE:
<223> OTHER INFORMATION: Antibody Epitopes on Milk Allergens

<400> SEQUENCE: 14

Cys Lys Glu Val Val Arg Asn Ala Asn Glu Glu Glu Tyr Ser
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Antibody Epitopes on Milk Allergens

<400> SEQUENCE: 15

Gln Thr Pro Val Val Val Pro Pro Phe Leu Gln Pro Glu Val
 1               5                  10
```